US008908756B2

(12) United States Patent
Kawasaki et al.

(10) Patent No.: US 8,908,756 B2
(45) Date of Patent: Dec. 9, 2014

(54) IMAGE TRANSMISSION APPARATUS AND IMAGE RECEPTION APPARATUS

(75) Inventors: Shinya Kawasaki, Sagamihara (JP); Takemitsu Honda, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 275 days.

(21) Appl. No.: 13/375,334

(22) PCT Filed: Apr. 22, 2010

(86) PCT No.: PCT/JP2010/002932
§ 371 (c)(1),
(2), (4) Date: Nov. 30, 2011

(87) PCT Pub. No.: WO2010/146760
PCT Pub. Date: Dec. 23, 2010

(65) Prior Publication Data
US 2012/0134410 A1    May 31, 2012

(30) Foreign Application Priority Data

Jun. 15, 2009  (JP) ................ 2009-142117

(51) Int. Cl.
  *H04N 7/18*     (2006.01)
  *A61B 1/00*     (2006.01)
  *A61B 5/00*     (2006.01)
(52) U.S. Cl.
  CPC ............ *H04N 7/183* (2013.01); *A61B 1/00016* (2013.01); *A61B 5/7232* (2013.01); *A61B 1/00036* (2013.01)
  USPC ........... 375/240; 600/109; 600/111; 600/150; 600/160; 600/179; 348/65

(58) Field of Classification Search
  CPC ................................... A61B 1/00016
  USPC ........................................ 375/240.1
  See application file for complete search history.

(56) References Cited

U.S. PATENT DOCUMENTS 7,060,027 B2 *  6/2006  Maeda et al. ............. 600/150
7,126,129 B2 * 10/2006  Yamamoto ............. 250/370.09
(Continued)

FOREIGN PATENT DOCUMENTS

| EP | 0 979 009 A2 | 2/2000 |
| EP | 2 421 244 A1 | 2/2012 |
| JP | 6-335450 A | 12/1994 |
| JP | 2000-123274 A | 4/2000 |

(Continued)

OTHER PUBLICATIONS

Japanese Office Action dated May 21, 2013, issued in corresponding Japanese Patent Application No. 2009-142117 with English translation (3 pages).

(Continued)

*Primary Examiner* — William C Vaughn, Jr.
*Assistant Examiner* — Luis M Perez
(74) *Attorney, Agent, or Firm* — Westerman, Hattori, Daniels & Adrian, LLP

(57) ABSTRACT

An image transmission apparatus may include a transmission unit that transmits a moving image compressed by lossy compression as first image data to an external apparatus through wireless communication, the transmission unit transmitting image data corresponding to one image in the moving image as second image data, the second image data being image data compressed at a lower compression rate than the lossy compression or not compressed, an instructing unit that outputs a disconnection signal to disconnect the wireless communication in response to an external manipulation, and a control unit that receives the disconnection signal from the instructing unit, the control unit controlling to disconnect the wireless communication in the transmission unit after the transmission of the second image data in the transmission unit has been completed.

12 Claims, 15 Drawing Sheets

(56) References Cited

U.S. PATENT DOCUMENTS

| | | | |
|---|---|---|---|
| 7,442,166 B2 * | 10/2008 | Huang et al. | 600/160 |
| 7,549,958 B2 * | 6/2009 | Hirata | 600/179 |
| 8,016,747 B2 * | 9/2011 | Sawachi | 600/111 |
| 8,125,515 B2 * | 2/2012 | Hibi | 348/65 |
| 8,545,396 B2 * | 10/2013 | Cover et al. | 600/109 |
| 2004/0225185 A1 | 11/2004 | Obata et al. | |
| 2006/0092029 A1 | 5/2006 | Browne et al. | |
| 2006/0209185 A1 * | 9/2006 | Yokoi | 348/65 |
| 2006/0242340 A1 | 10/2006 | Ono | |
| 2008/0015415 A1 | 1/2008 | Obata et al. | |
| 2008/0045789 A1 * | 2/2008 | Sawachi | 600/111 |

FOREIGN PATENT DOCUMENTS

| | | |
|---|---|---|
| JP | 2002-359874 A | 12/2002 |
| JP | 2005-176223 A | 6/2005 |
| JP | 2005-176233 A | 6/2005 |
| JP | 2009-069855 A | 4/2009 |
| WO | 2008/063565 A2 | 5/2008 |

OTHER PUBLICATIONS

International Search Report of PCT/JP2010/002932, mailing date May 25, 2010.

Extended European Search Report dated Jan. 21, 2013, issued in corresponding European patent application No. 10789145.9.

* cited by examiner

IMAGE TRANSMISSION APPARATUS AND IMAGE RECEPTION APPARATUS

TECHNICAL FIELD

The present invention relates to an image transmission apparatus and an image reception apparatus.

Priority is claimed on Japanese Patent Application No. 2009-142117, filed Jun. 15, 2009, the content of which is incorporated herein by reference.

BACKGROUND ART

In recent years, as early detection and diagnostic accuracy for lesions using endoscope examination has been improved and various treatment tools included in an endoscope have been developed, further performance improvement of the endoscope is highly expected. However, image data of the inside of a coelom imaged by the endoscope is communicated to a display device, which is provided in a position away from the endoscope, via an image transmission cable (hereinafter referred to as cable). Thereby, a positional relationship among a surgeon, a subject, and the display device is limited due to the cable.

An endoscope that overcomes the limitation of a positional relationship among a surgeon, a subject and a display device by wirelessly transmitting data of an image acquired by image pickup using the endoscope to the display device has been proposed (e.g., see Patent Document 1).

Here, when moving image data of the inside of a coelom acquired by image pickup using the endoscope is compressed and the compressed moving image data is transmitted from the endoscope to the display device, the moving image data is usually encoded by rearranging an image frame order (hereinafter referred to as reordering) in a moving image data compression process, such as MPEG (Moving Picture Experts Group). This requires, for example, an input waiting time for image frame data in the compression process. Accordingly, a delay of a display time (hereinafter referred to as display delay) occurs between an actual motion in the coelom and a displayed moving image.

However, if a still image of the inside of the coelom is acquired by image pickup, it is difficult for a surgeon, who is manipulating the endoscope while watching the moving image transmitted from the endoscope, to accurately recognize image pickup timing for the still image as a display delay between an actual motion of an object to be imaged and a displayed moving image increases. Because of this, for the moving image data transmitted from the endoscope to the display device, it is desirable for reduction of the display delay to be prior to reduction of a data size. In a normal endoscope, a display delay of moving image data transmitted from the endoscope to a display device is reduced by using only an intra-frame compression process, such as I picture of MPEG or Motion-JPEG 2000, to eliminate reordering causing the display delay.

Meanwhile, with the improved early detection and diagnostic accuracy for lesions, high image quality is necessary for the still image data acquired by image pickup using the endoscope. Thereby, the still image data acquired by image pickup using the endoscope needs to be uncompressed data, lossless compression data without data loss caused by a decompression process, or lossy low compressed data with less data loss caused by the decompression process.

For the moving image data, since image frames are continuously updated, degradation of image quality is not particularly conspicuous, while for the still image data in which image frames are not updated, the degradation of the image quality is conspicuous, as seen from a comparison between the same image frames. Accordingly, the still image data needs to have higher image quality than the moving image data.

CITATION LIST

Patent Document 1: Japanese Unexamined Patent Application, First Publication, No. H6-335450

SUMMARY OF INVENTION

Problems to be Solved by the Invention

However, since high-definition still image data has a large data size, time is taken for communication. Accordingly, communication of the still image data may not be completed when the endoscope examination ends. In such a case, a user who has failed to recognize that the communication has not been completed is likely to turn off the power of the endoscope or the reception apparatus.

The present invention has been invented in view of the foregoing circumstances, and an object of the present invention is to provide an image transmission apparatus and an image reception apparatus capable of reliably acquiring high-definition still image data taking time for communication.

Means for Solving the Problems

An image transmission apparatus in accordance with the present invention may include: a transmission unit that transmits a moving image compressed by lossy compression as first image data to an external apparatus through wireless communication, the transmission unit transmitting image data corresponding to one image in the moving image as second image data, the second image data being image data compressed at a lower compression rate than the lossy compression or not compressed; an instructing unit that outputs a disconnection signal to disconnect the wireless communication in response to an external manipulation; and a control unit that receives the disconnection signal from the instructing unit, the control unit controlling to disconnect the wireless communication in the transmission unit after the transmission of the second image data in the transmission unit has been completed.

The control unit may immediately disconnect the wireless communication if the control unit receives a disconnection signal, which has been output from the instructing unit, during transmission of the first image data.

The image transmission apparatus in accordance with the present invention may further include a power supply unit that supplies power to the apparatus. The control unit may control to stop power supply from the power supply unit after the control unit receives the disconnection signal from the instructing unit and the transmission of the second image data in the transmission unit has been completed.

An image reception apparatus in accordance with the present invention may include: a reception unit that receives a moving image compressed by lossy compression as first image data from an external apparatus through wireless communication, the reception unit receiving image data corresponding to one image in the moving image as second image data, the second image data being image data compressed at a lower compression rate than the lossy compression or not compressed; an instructing unit that outputs a disconnection signal to disconnect the wireless communication in response to an external manipulation; and a control unit that controls to disconnect the wireless communication in the reception unit after the control unit receives the disconnection signal from the instructing unit and the reception of the second image data in the reception unit has been completed.

Effect of the Invention

According to the present invention, the image transmission terminal and the image reception terminal disconnect the communication after the image reception terminal completes reception of image data, thereby reliably acquiring high-definition still image data taking time for communication.

BEST MODE FOR CARRYING OUT THE INVENTION

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

First Preferred Embodiment

Figure 1:
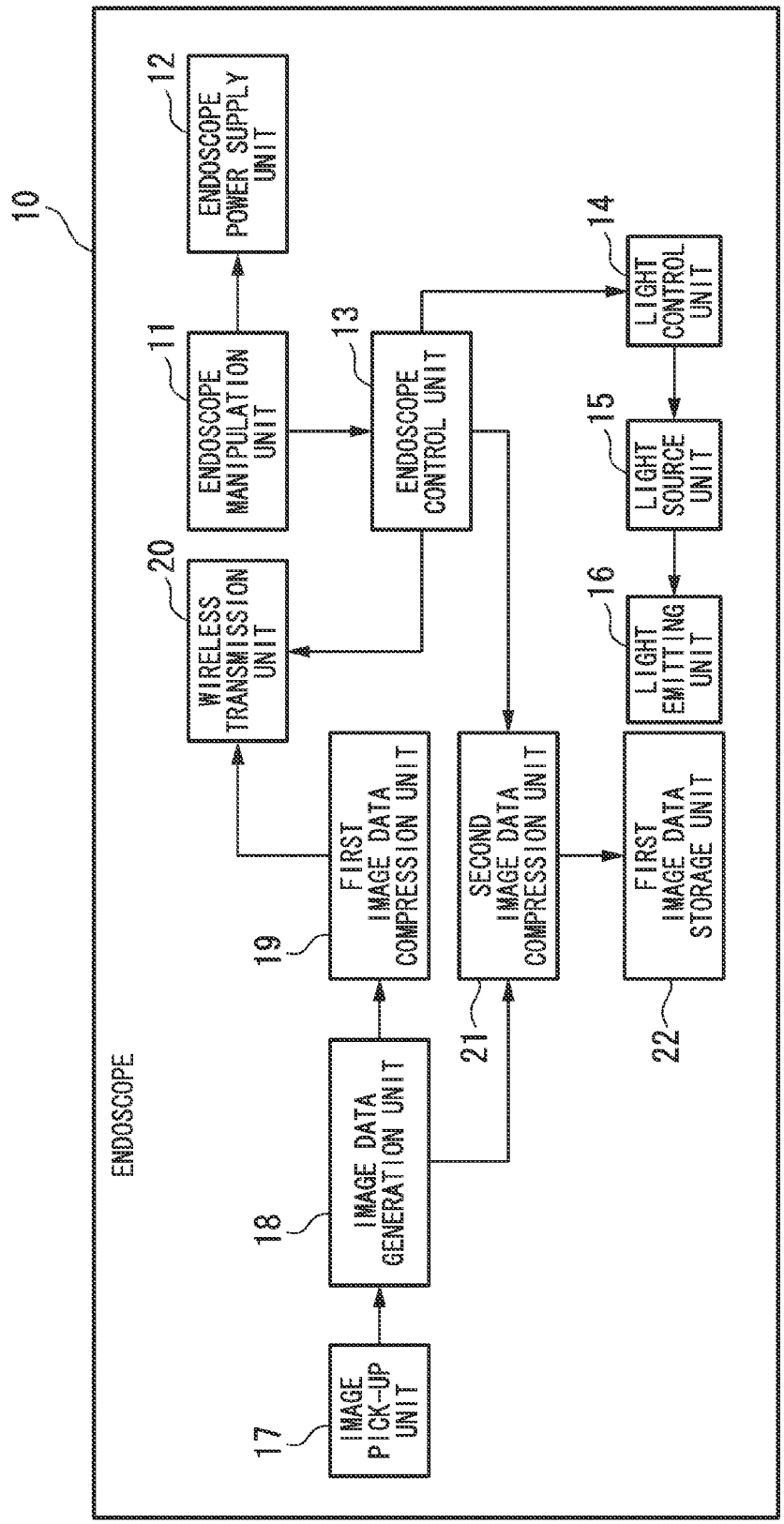
FIG. 1 is a block diagram illustrating an endoscope (image transmitting terminal) in accordance with a first preferred embodiment of the present.

Next, a preferred embodiment of the present invention will be described in detail with reference to the accompanying drawings. FIG. 1 is a block diagram illustrating an endoscope (image transmitting terminal) in accordance with the first preferred embodiment of the present. In FIG. 1, an endoscope 10 includes an endoscope manipulation unit 11, an endoscope power supply unit 12, an endoscope control unit 13, a light control unit 14, a light source unit 15, a light emitting unit 16, an image pickup unit 17, an image data generation unit 18, a first image data compression unit 19, a wireless transmission unit 20, a second image data compression unit 21, and a first image data storage unit 22.

The endoscope manipulation unit 11 receives a manipulation input from a surgeon (user), and outputs a manipulation signal to the endoscope control unit 13 and the endoscope power supply unit 12. The endoscope power supply unit 12 receives a communication connection instruction as the manipulation signal from the endoscope manipulation unit 11. If the endoscope power supply unit 12 receives the communication connection instruction, the endoscope power supply unit 12 initiates power supply to each block of the endoscope 10. The endoscope power supply unit 12 also receives a communication disconnection instruction as the manipulation signal from the endoscope manipulation unit 11. If the endoscope power supply unit 12 receives the communication disconnection instruction, the endoscope power supply unit 12 stops the power supply to each block of the endoscope 10 when a given amount of time has elapsed after the endoscope power supply unit 12 receives the communication disconnection instruction. Further, the time at which the endoscope power supply unit 12 stops the power supply may be instructed by the endoscope control unit 13.

The endoscope control unit 13 receives emission amount data for light irradiated into a coelom as the manipulation signal from the endoscope manipulation unit 11, and outputs the emission amount data to the light control unit 14. Further, if the endoscope control unit 13 receives the communication connection instruction as the manipulation signal from the endoscope manipulation unit 11, the endoscope control unit 13 outputs an instruction for communication connection with a wireless reception unit 34 of a display device 30 shown in FIG. 2, which will be described later, to the wireless transmission unit 20. Meanwhile, if the endoscope control unit 13 receives the communication disconnection instruction as the manipulation signal from the endoscope manipulation unit 11, the endoscope control unit 13 outputs an instruction for communication disconnection from the wireless reception unit 34 of the display device 30 to the wireless transmission unit 20.

The endoscope control unit 13 receives a low (un-) compressed data generation instruction (e.g., a still-image acquisition instruction) as the manipulation signal from the endoscope manipulation unit 11, and outputs the low (un-) compressed data generation instruction to the second image data compression unit 21. Further, the endoscope control unit 13 may include a storage unit (not shown) for storing, for example, parameters used for program operation.

The image pickup unit 17 includes, for example, a solid-state image pickup device such as a CCD (Charge Coupled Device) image sensor (hereinafter referred to as a CCD) or a CMOS (Complementary Metal Oxide Semiconductor) image sensor (hereinafter referred to as a CMOS). The image pickup unit 17 outputs a pixel signal corresponding to an amount of light incident to the solid-state image pickup device to the image data generation unit 18. The image data generation unit 18 generates image frame data based on the pixel signal input from the image pickup unit 17, and outputs the image frame data to the first image data compression unit 19 and the second image data compression unit 21.

The first image data compression unit 19 intra-frame-compresses the image frame data at a high compression rate, and continuously outputs the compressed image frame data as moving image data to the wireless transmission unit 20.

If the wireless transmission unit 20 receives the communication connection instruction from the endoscope control unit 13, the wireless transmission unit 20 initiates packet communication with the wireless reception unit 34 of the display device 30 shown in FIG. 2, which will be described later. Further, the wireless transmission unit 20 performs a modulation process on the compressed image frame data input from the first image data compression unit 19 and transmits packet data of the image frame data as a wireless signal to the wireless reception unit 34 of the display device 30 shown in FIG. 2, which will be described later. On the other hand, if the wireless transmission unit 20 receives the communication disconnection instruction from the endoscope control unit 13, the wireless transmission unit 20 terminates the packet communication with the wireless reception unit 34 of the display device 30 shown in FIG. 2, which will be described later.

If the second image data compression unit 21 receives the low (un-) compressed data generation instruction from the endoscope control unit 13, the second image data compression unit 21 intra-frame-compresses the image frame data at a low compression rate, and outputs the compressed image frame data as still image data to the first image data storage unit 22. Here, the compressed image frame data output by the second image data compression unit 21 is low compressed data with less data loss than the compressed image frame data output by the first image data compression unit 19, so that the image frame data has high image quality when the image frame data is decompressed. Further, the second image data compression unit 21 may output uncompressed data or may output lossless compression data with no data loss.

The first image data storage unit 22 receives and stores the compressed image frame data from the second image data compression unit 21. The first image data storage unit 22 may be, for example, a detachable recording medium such as a memory card. The first image data storage unit 22 may include an external interface (not shown) therein and may convert the compressed image frame data into data suitable for protocol for a peripheral device (not shown) of the endoscope 10 and then output the compressed image frame data to the peripheral device (not shown).

The light control unit 14 drives the light source unit 15 based on the emission amount data input from the endoscope control unit 13. The light source unit 15 includes, for example, a light emitting device such as an LED (Light Emitting Diode), and supplies light to the light emitting unit 16, for example, via an optical fiber as driven by the light control unit 14. The light emitting unit 16 irradiates the supplied light into the coelom.

Figure 2:
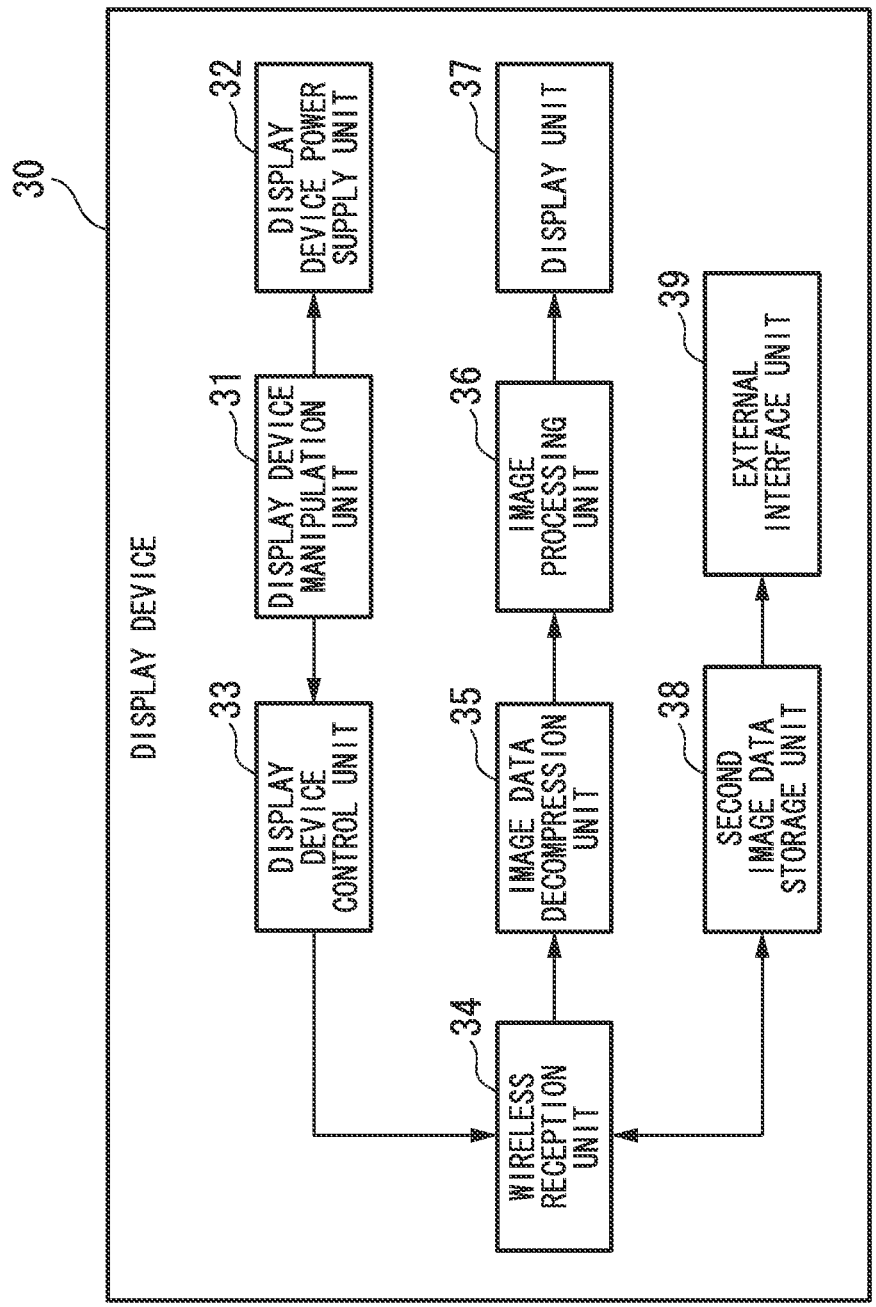
FIG. 2 is a block diagram illustrating a display device in accordance with the first preferred embodiment of the present invention.

FIG. 2 is a block diagram illustrating the display device in accordance with the first preferred embodiment of the present invention. In FIG. 2, the display device 30 includes a display device manipulation unit 31, a display device power supply unit 32, a display device control unit 33, the wireless reception unit 34, an image data decompression unit 35, an image processing unit 36, a display unit 37, a second image data storage unit 38, and an external interface unit 39.

The display device manipulation unit 31 receives a manipulation input from the surgeon, and outputs a manipulation signal to the display device control unit 33 and the display device power supply unit 32. The display device power supply unit 32 receives a communication connection instruction as the manipulation signal from the display device manipulation unit 31. If the display device power supply unit 32 receives the communication connection instruction, the display device power supply unit 32 initiates power supply to each block of the display device 30. Also, the display device power supply unit 32 receives a communication disconnection instruction as the manipulation signal from the display device manipulation unit 31. If the display device power supply unit 32 receives the communication disconnection instruction, the display device power supply unit 32 stops the power supply to each block of the display device 30 when a given amount of time has elapsed after receiving the communication disconnection instruction. Further, a time at which the display device power supply unit 32 stops the power supply may be instructed by the display device control unit 33.

If the display device control unit 33 receives a communication connection instruction as the manipulation signal from the display device manipulation unit 31, the display device control unit 33 outputs an instruction for a communication connection with the wireless transmission unit 20 of the endoscope 10 to the wireless reception unit 34. On the other hand, if the display device control unit 33 receives a communication disconnection instruction as the manipulation signal from the display device manipulation unit 31, the display device control unit 33 outputs an instruction for a communication disconnection from the wireless transmission unit 20 of the endoscope 10 to the wireless reception unit 34.

If the wireless reception unit 34 receives the communication connection instruction from the display device control unit 33, the wireless reception unit 34 initiates packet communication with the wireless transmission unit 20 of the endoscope 10. Further, the wireless reception unit 34 performs a demodulation process on data received as a wireless signal from the endoscope 10 to acquire, from the packet data, the compressed image frame data transmitted from the wireless transmission unit 20 of the endoscope 10, and outputs the compressed image frame data to the image data decompression unit 35 and the second image data storage unit 38. On the other hand, if the wireless reception unit 34 receives the communication disconnection instruction from the display device control unit 33, the wireless reception unit 34 terminates the packet communication with the wireless transmission unit 20 of the endoscope 10.

The image data decompression unit 35 decompresses the input compressed image frame data, and outputs the decompressed image frame data to the image processing unit 36. The image processing unit 36 performs image processing such as noise reduction or an enhancement process on the decompressed image frame data, and outputs the processed-image frame data to the display unit 37. The display unit 37 displays the processed image frame data as an image, for example, on a display.

The second image data storage unit 38 stores the compressed image frame data input from the wireless reception unit 34. The external interface unit 39 acquires the compressed image frame data from the second image data storage unit 38, converts the compressed image frame data into data suitable for protocol with a peripheral device (not shown) of the display device 30, and then outputs the compressed image frame data to the peripheral device (not shown).

Figure 3:
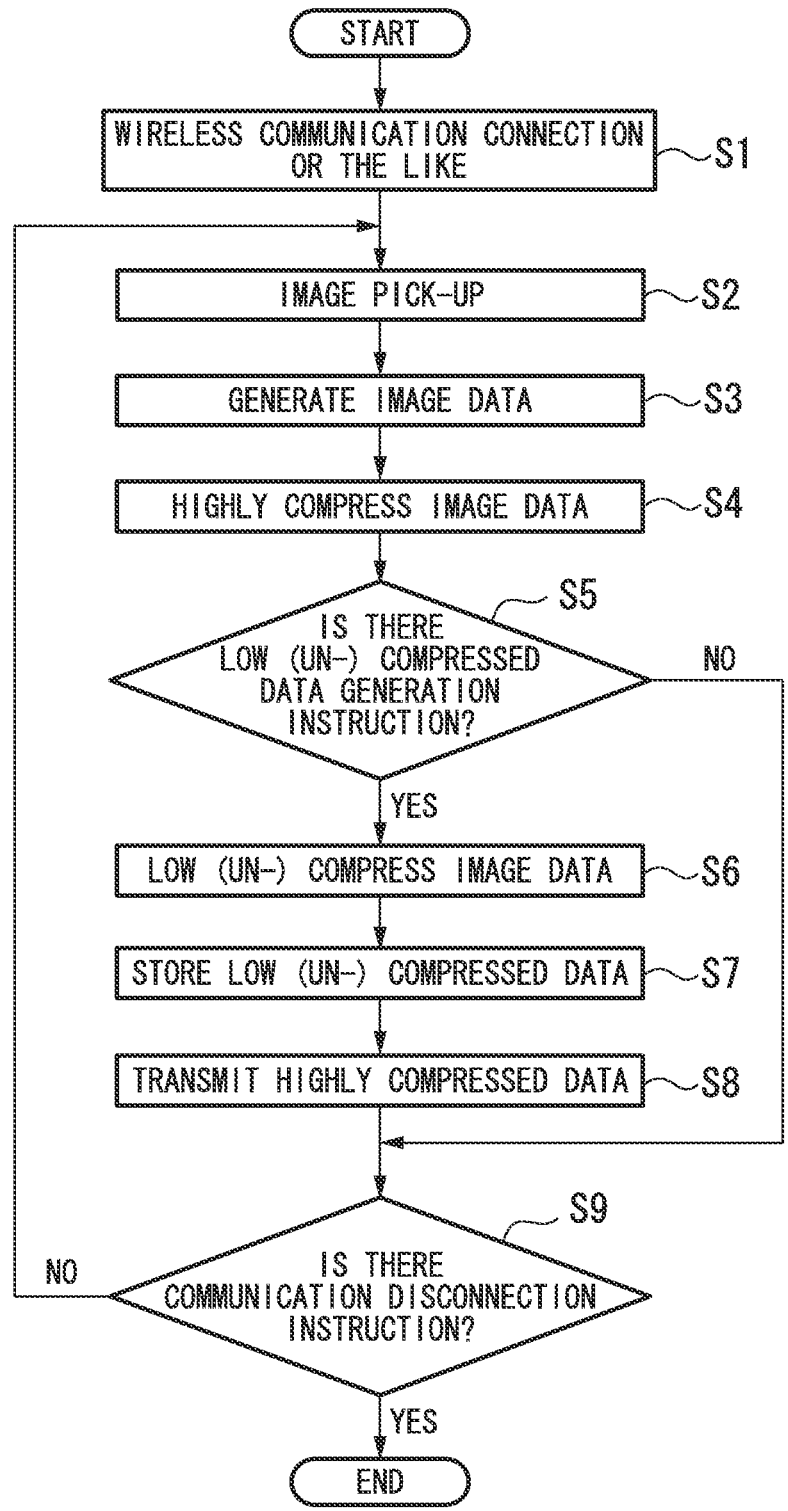
FIG. 3 is a flowchart illustrating operation of the endoscope in accordance with the first preferred embodiment of the present invention.

FIG. 3 is a flowchart illustrating operation of the endoscope in accordance with the first preferred embodiment of the present invention. The endoscope manipulation unit 11 receives a manipulation input from a surgeon and outputs a manipulation signal to the endoscope control unit 13 and the endoscope power supply unit 12. The endoscope power supply unit 12 receives a communication connection instruction as the manipulation signal from the endoscope manipulation unit 11 and initiates power supply to each block of the endoscope 10.

The endoscope control unit 13 receives emission amount data for light irradiated into a coelom as the manipulation signal from the endoscope manipulation unit 11, and outputs the emission amount data to the light control unit 14. The light control unit 14 drives the light source unit 15 based on the emission amount data input from the endoscope control unit 13. The light source unit 15 supplies light to the light emitting unit 16, for example, via an optical fiber as driven by the light control unit 14. The light emitting unit 16 irradiates the supplied light into the coelom.

The endoscope control unit 13 receives a communication connection instruction as the manipulation signal from the endoscope manipulation unit 11, and outputs an instruction for a communication connection with the wireless reception unit 34 of the display device 30 to the wireless transmission unit 20. The wireless transmission unit 20 receives the communication connection instruction from the endoscope control unit 13 and initiates packet communication with the wireless reception unit 34 of the display device 30 (step S1).

The power-supplied image pickup unit 17 outputs a pixel signal corresponding to an amount of light incident to the solid-state image pickup device to the image data generation unit 18 (step S2). The image data generation unit 18 generates image frame data based on the pixel signal input from the image pickup unit 17 and outputs the image frame data to the first image data compression unit 19 and the second image data compression unit 21 (step S3). The first image data compression unit 19 outputs the intra-frame-compressed image frame data to the wireless transmission unit 20 (step S4).

The endoscope control unit 13 determines whether a low (un-) compressed data generation instruction (e.g., a still-image acquisition instruction) is received from the endoscope manipulation unit 11 (step S5). If the endoscope control unit 13 does not receive a low (un-) compressed data generation instruction as the manipulation signal from the endoscope manipulation unit 11, the endoscope control unit 13 proceeds to step S9.

If the endoscope control unit 13 receives the low (un-) compressed data generation instruction as the manipulation signal from the endoscope manipulation unit 11, the endoscope control unit 13 outputs the low (un-) compressed data generation instruction to the second image data compression unit 21. If the second image data compression unit 21 receives the low (un-) compressed data generation instruction, the second image data compression unit 21 outputs the intra-frame-compressed image frame data to the first image data storage unit 22 (step S6). The first image data storage unit 22 receives and stores the intra-frame-compressed image frame data (low (un-) compressed data) from the second image data compression unit 21 (step S7).

The wireless transmission unit 20 performs a modulation process on the compressed image frame data (highly compressed data) input from the first image data compression unit 19, and transmits packet data of the image frame data as a wireless signal to the wireless reception unit 34 of the display device 30 (step S8). If the wireless transmission unit 20 receives the communication disconnection instruction, the wireless transmission unit 20 terminates the packet communication with the wireless reception unit 34 of the display device 30. On the other hand, if the wireless transmission unit 20 does not receive the communication disconnection instruction, the wireless transmission unit 20 returns to step S2. Further, the endoscope power supply unit 12 determines whether the communication disconnection instruction is received as the manipulation signal from the endoscope manipulation unit 11. If the endoscope power supply unit 12 receives the communication disconnection instruction, the endoscope power supply unit 12 stops the power supply to each block of the endoscope 10 after a given amount of time has elapsed. If the endoscope power supply unit 12 does not receive the communication disconnection instruction, the endoscope power supply unit 12 returns to step S2 (step S9).

Figure 4:
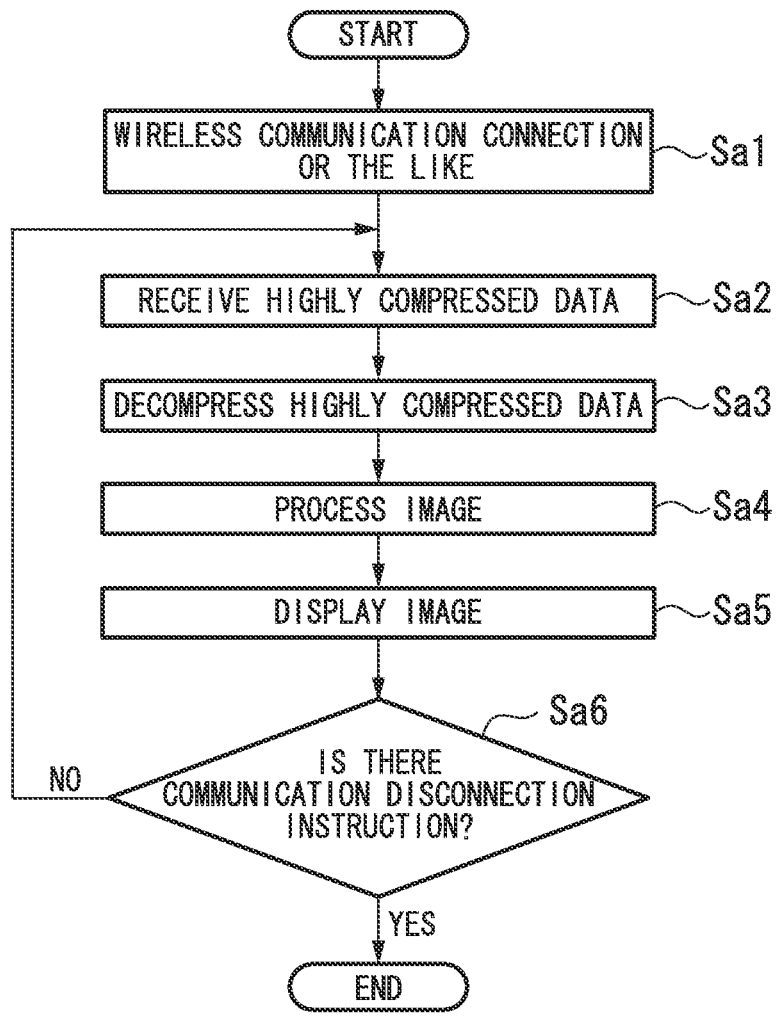
FIG. 4 is a flowchart illustrating operation of the display device in accordance with the first preferred embodiment of the present invention.

FIG. 4 is a flowchart illustrating operation of the display device in accordance with the first preferred embodiment of the present invention. The display device manipulation unit 31 receives a manipulation input from a surgeon, and outputs a manipulation signal to the display device control unit 33 and the display device power supply unit 32. The display device power supply unit 32 receives a communication connection instruction as the manipulation signal from the display device manipulation unit 31, and initiates power supply to each block of the display device 30.

The display device control unit 33 receives a communication connection instruction as the manipulation signal from the display device manipulation unit 31 and outputs an instruction for a communication connection with the wireless transmission unit 20 of the endoscope 10 to the wireless reception unit 34. The wireless reception unit 34 receives the communication connection instruction from the display device control unit 33, and initiates packet communication with the wireless transmission unit 20 of the endoscope 10 (step Sa1).

The wireless reception unit 34 performs a demodulation process on the data received as a wireless signal to acquire, from the packet data, the compressed image frame data (highly compressed data) transmitted from the wireless transmission unit 20 of the endoscope 10, and outputs the compressed image frame data to the image data decompression unit 35 and the second image data storage unit 38 (step Sa2). The image data decompression unit 35 decompresses the input compressed image frame data (highly compressed data) and outputs the decompressed image frame data to the image processing unit 36 (step Sa3). The image processing unit 36 performs image processing on the decompressed image frame data and outputs the processed image frame data to the display unit 37 (step Sa4). The display unit 37 displays the processed image frame data as an image, for example, on a display (step Sa5).

If the wireless reception unit 34 receives a communication disconnection instruction, the wireless reception unit 34 terminates the packet communication with the wireless transmission unit 20 of the endoscope 10. On the other hand, if the wireless reception unit 34 does not receive the communication disconnection instruction, the wireless reception unit 34 returns to step Sa2. Further, the display device power supply unit 32 determines whether the display device power supply unit 32 receives the communication disconnection instruction as the manipulation signal from the display device manipulation unit 31. If the display device power supply unit 32 receives the communication disconnection instruction, the display device power supply unit 32 stops the power supply to each block of the display device 30 after a given time has elapsed. If the display device power supply unit 32 does not receive the communication disconnection instruction, the display device power supply unit 32 returns to step Sa2 (step Sa6).

Thus, since the wireless transmission unit 20 of the endoscope 10 does not wirelessly transmit the low (un-) compressed data (e.g., still image data) having a great data size, the wireless transmission unit 20 can wirelessly transmit highly compressed data (e.g., moving image data) to the display device 30 without causing a decrease in the communication speed. Further, since the endoscope 10 stores the low (un-) compressed data having a great data size in the first image data storage unit 22 included in the endoscope 10, the surgeon can obtain high-definition still image data with the endoscope 10. Further, the surgeon can display the wirelessly transmitted moving image data on the display unit 37 of the display device 30 and simultaneously obtain the moving image data from the external interface unit 39.

Alternatively, the low (un-) compressed data generation instruction (e.g., still-image acquisition instruction) may be transmitted from the wireless transmission unit 20 of the endoscope 10 to the wireless reception unit 34 of the display device 30, and the display device 30 receiving the low (un-) compressed data generation instruction may suspend update of image frame data (e.g., moving image data) displayed on the display unit 37. This enables the endoscope 10 to notify the surgeon that a low (un-) compressed data generation process is performed.

Second Preferred Embodiment

Figure 5:
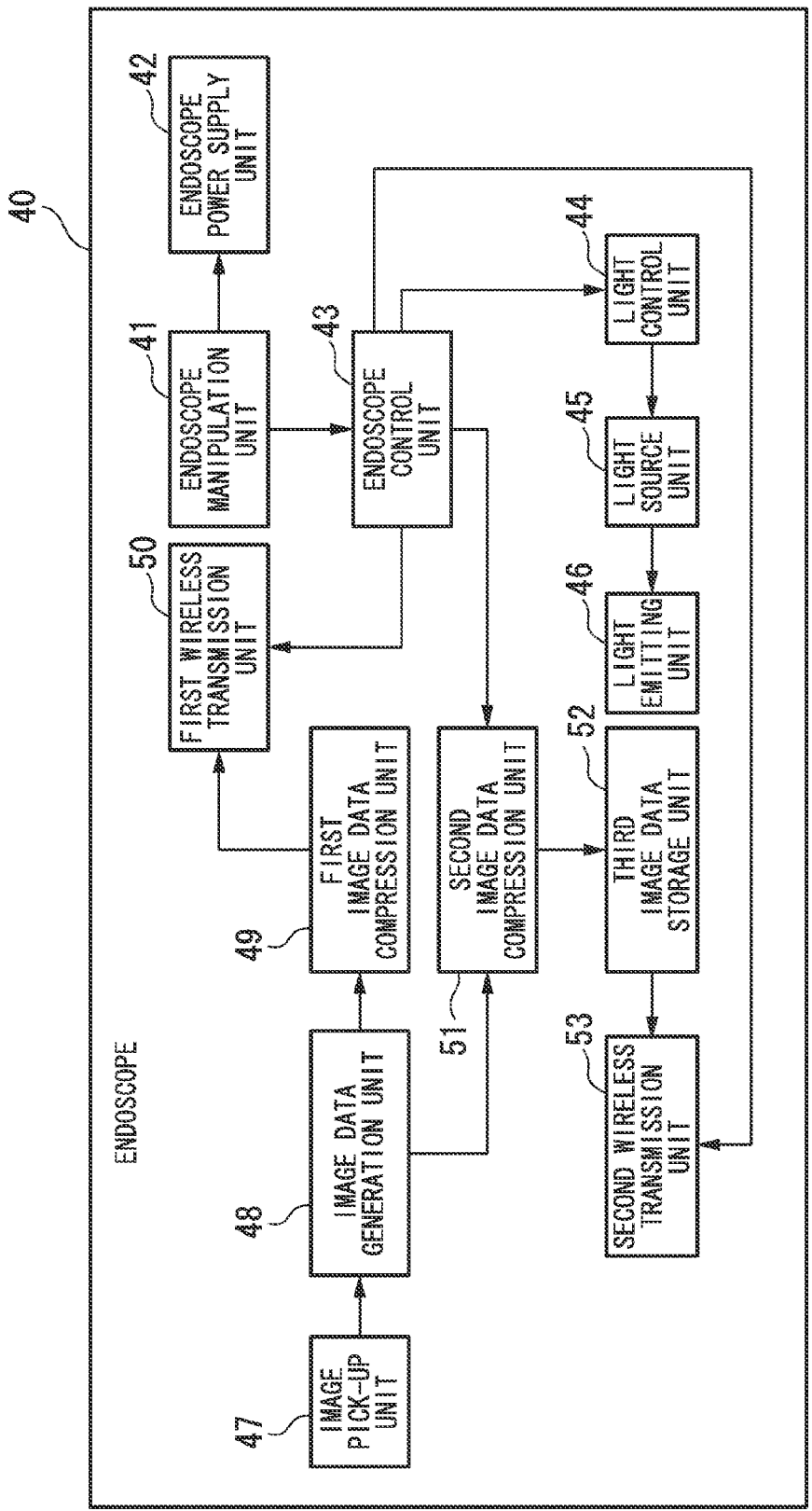
FIG. 5 is a block diagram illustrating an endoscope in accordance with a second preferred embodiment of the present invention.

Next, a second preferred embodiment of the present invention will be described. FIG. 5 is a block diagram illustrating an endoscope in accordance with the second preferred embodiment of the present invention. In FIG. 5, an endoscope 40 includes an endoscope manipulation unit 41, an endoscope power supply unit 42, an endoscope control unit 43, a light control unit 44, a light source unit 45, a light emitting unit 46, an image pickup unit 47, an image data generation unit 48, a first image data compression unit 49, a first wireless transmission unit 50, a second image data compression unit 51, a third image data storage unit 52, and a second wireless transmission unit 53.

The endoscope manipulation unit 41 performs the same operation as the endoscope manipulation unit 11 in FIG. 1. The endoscope power supply unit 42 performs the same operation as the endoscope power supply unit 12 in FIG. 1. The endoscope control unit 43 performs the same operation as the endoscope control unit 13 in FIG. 1. The endoscope control unit 43 outputs an instruction for a communication connection with a first wireless reception unit 64 of a display device 60 shown in FIG. 6, which will be described later, to the first wireless transmission unit 50. Similarly, the endoscope control unit 43 outputs an instruction for a communication connection with a second wireless reception unit 68 of the display device 60 shown in FIG. 6, which will be described later, to the second wireless transmission unit 53. The endoscope control unit 43 receives a communication connection instruction as a manipulation signal from the endoscope manipulation unit 41 of the endoscope 40. For a communication disconnection instruction, the endoscope control unit 43 operates similar to the endoscope control unit 13 in FIG. 1.

The endoscope control unit 43 indicates a packet data transmission time to the first wireless transmission unit 50 and the second wireless transmission unit 53. Further, the endoscope control unit 43 acquires, from the first wireless transmission unit 50, information indicating whether the first wireless transmission unit 50 has completed the packet data transmission. Similarly, the endoscope control unit 43 acquires, from the second wireless transmission unit 53, information indicating whether the second wireless transmission unit 53 had completed packet data transmission.

If a low (un-) compressed data generation instruction (e.g., a still-image acquisition instruction) is received from the endoscope manipulation unit 41 as a manipulation signal, the endoscope control unit 43 outputs the low (un-) compressed data generation instruction to the second image data compression unit 51. Further, the endoscope control unit 43 instructs the first wireless transmission unit 50 to add "highly compressed data storage instruction information" to the image frame data. Here, the "highly compressed data storage instruction information" is information referenced by the first wireless reception unit 64 of the display device 60 in order to store the image frame data from the first wireless transmission unit 50 in a fourth image data storage unit 69 of the display device 60 shown in FIG. 6, which will be described later. Alternatively, the "highly compressed data storage instruction information" may be originally contained in the image frame data instead of being added to the image frame data, and "enable" and "disable" of a bit indicating the "highly compressed data storage instruction information" may be switched.

The endoscope control unit 43 having received the low (un-) compressed data generation instruction may instruct the first wireless transmission unit 50 to suspend packet data transmission of the first wireless transmission unit 50 until the packet data transmission of the second wireless transmission unit 53 has been completed, so that the second wireless transmission unit 53 transmits the packet data during a time in which the packet data transmission of the first wireless transmission unit 50 is suspended.

The light control unit 44, the light source unit 45, and the light emitting unit 46 perform the same operations as the light control unit 14, the light source unit 15, and the light emitting unit 16 in FIG. 1, respectively. The image pickup unit 47 performs the same operation as the image pickup unit 17 in FIG. 1. The image data generation unit 48 performs the same operation as the image data generation unit 18 in FIG. 1.

The first image data compression unit 49 performs the same operation as the first image data compression unit 19 in FIG. 1. The first image data compression unit 49 outputs intra-frame-compressed image frame data (e.g., moving image data) to the first wireless transmission unit 50.

The first wireless transmission unit 50 performs the same operation as the wireless transmission unit 20 in FIG. 1. The first wireless transmission unit 50 transmits packet data of the image frame data as a wireless signal to the first wireless reception unit 64 of the display device 60 shown in FIG. 6, which will be described later. Further, if the first wireless transmission unit 50 receives a "highly compressed data storage instruction information" addition instruction from the endoscope control unit, the first wireless transmission unit 50 adds the "highly compressed data storage instruction information" to the image frame data and transmits the packet data.

The second image data compression unit 51 performs the same operation as the second image data compression unit 21 in FIG. 1. The second image data compression unit 51 outputs the intra-frame-compressed image frame data (e.g., still image data) to the third image data storage unit 52. Here, in order to obtain high image quality even after decompression, the compressed image frame data output by the second image data compression unit 51 is low compressed data with less data loss than the compressed image frame data output by the first image data compression unit 49. Alternatively, the second image data compression unit 51 may output uncompressed data or may output lossless compression data without data loss caused by the decompression process.

The third image data storage unit 52 corresponds to the first image data storage unit 22 in FIG. 1. The third image data storage unit 52 receives and stores the compressed image frame data from the second image data compression unit 51. The third image data storage unit 52 outputs the compressed image frame data to the second wireless transmission unit 53.

If the second wireless transmission unit 53 receives a communication connection instruction from the endoscope control unit 43, the second wireless transmission unit 53 initiates packet communication with a second wireless reception unit 68 of the display device 60 shown in FIG. 6, which will be described later. Further, the second wireless transmission unit 53 transmits packet data of the image frame data as a wireless signal to the second wireless reception unit 68 of the display device 60 shown in FIG. 6, which will be described later. On the other hand, if the second wireless transmission unit 53 receives the communication disconnection instruction from the endoscope control unit 43, the second wireless transmission unit 53 terminates the packet communication with the second wireless reception unit 68 of the display device 60 shown in FIG. 6, which will be described later.

Further, the second wireless transmission unit 53 need not perform the same communication scheme as the first wireless transmission unit 50, but may perform a higher speed communication than the first wireless transmission unit 50. For example, the second wireless transmission unit 53 may perform multilevel modulation to transmit much information in one section (symbol) of a signal. Further, the second wireless transmission unit 53 may have a broader communication bandwidth than the first wireless transmission unit 50.

Figure 6:
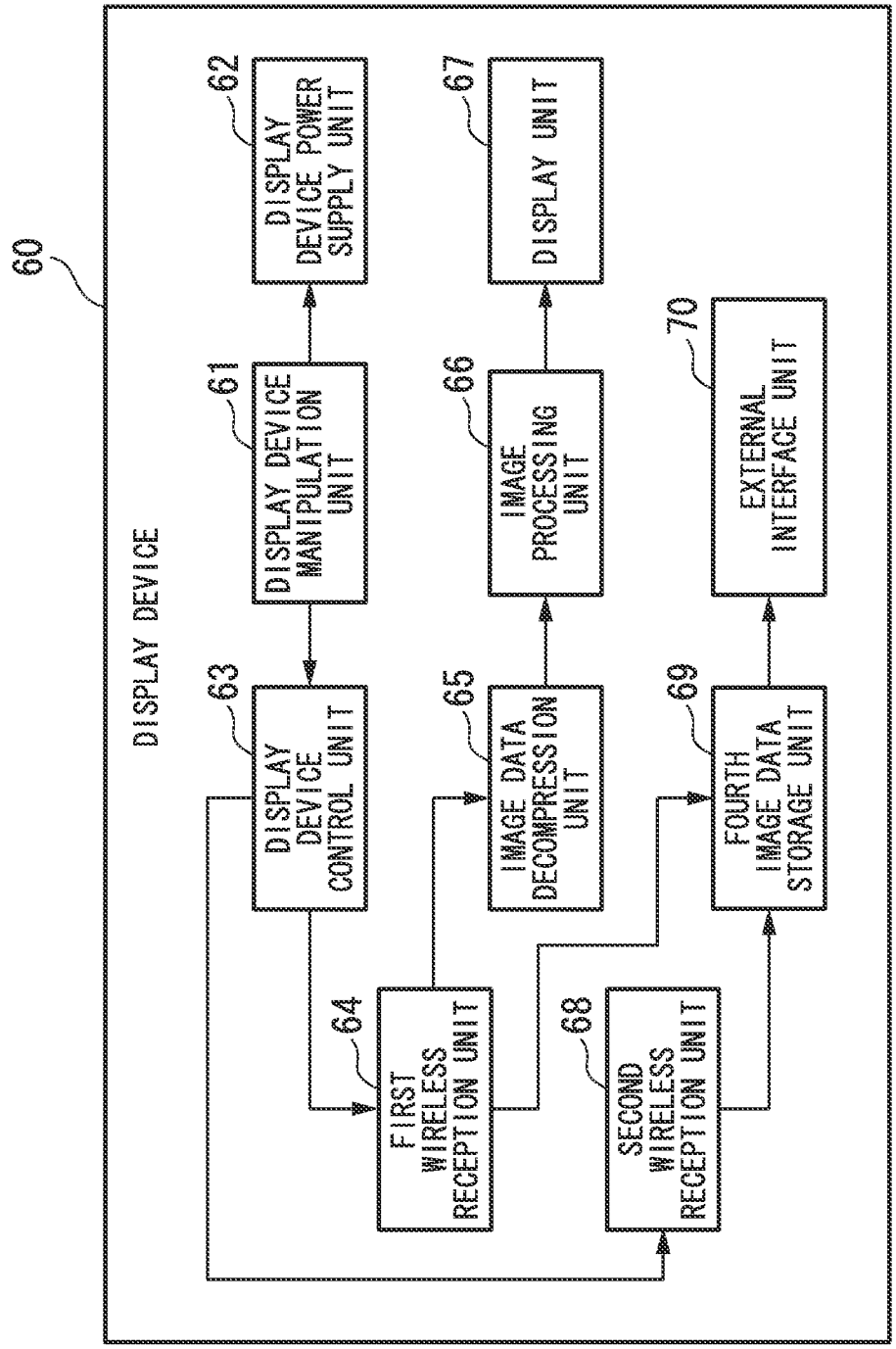
FIG. 6 is a block diagram illustrating a display device in accordance with the second preferred embodiment of the present invention.

FIG. 6 is a block diagram illustrating the display device in accordance with the second preferred embodiment of the present invention. In FIG. 6, the display device 60 includes a display device manipulation unit 61, a display device power supply unit 62, a display device control unit 63, the first wireless reception unit 64, an image data decompression unit 65, an image processing unit 66, a display unit 67, the second wireless reception unit 68, a fourth image data storage unit 69, and an external interface unit 70.

The display device manipulation unit 61 performs the same operation as the display device manipulation unit 31 in FIG. 2. The display device power supply unit 62 performs the same operation as the display device power supply unit 32 in FIG. 2. The display device control unit 63 performs the same operation as the display device control unit 33 in FIG. 2. The display device control unit 63 receives a communication connection instruction as a manipulation signal from the display device manipulation unit 61, and outputs an instruction for a communication connection with the first wireless transmission unit 50 of the endoscope 40 to the first wireless reception unit 64. Similarly, the display device control unit 63 outputs an instruction for a communication connection with the second wireless transmission unit 53 of the endoscope 40 to the second wireless reception unit 68. For a communication disconnection instruction, the display device control unit 63 operates similarly to the display device control unit 33 in FIG. 2.

The first wireless reception unit 64 receives a communication connection instruction from the display device control unit 63, and the first wireless reception unit 64 initiates packet communication with the first wireless transmission unit 50 of the endoscope 40. The first wireless reception unit 64 performs a demodulation process on the data received as a wireless signal to acquire, from the packet data, the compressed image frame data transmitted from the first wireless transmission unit 50 of the endoscope 40, and outputs the compressed image frame data to the image data decompression unit 65.

The first wireless reception unit 64 determines whether the "highly compressed data storage instruction information" has been added to the image frame data (highly compressed data) transmitted from the first wireless transmission unit 50 in FIG. 5. If the "highly compressed data storage instruction information" has been added, the first wireless reception unit 64 also outputs the compressed image frame data to the fourth image data storage unit 69.

The second wireless reception unit 68 receives a communication connection instruction from the display device control unit 63, and initiates packet communication with the second wireless transmission unit 53 of the endoscope 40. The second wireless reception unit 68 performs a demodulation process on the data received as a wireless signal to acquire, from the packet data, the compressed image frame data transmitted from the second wireless transmission unit 53 of the endoscope 40, and outputs the compressed image frame data to the fourth image data storage unit 69.

The image data decompression unit 65 decompresses the input compressed image frame data and outputs the decompressed image frame data to the image processing unit 66. The image processing unit 66 performs image processing such as noise reduction or an enhancement process on the decompressed image frame data, and outputs the processed image frame data to the display unit 67. The display unit 67 displays the processed image frame data as an image, for example, on a display.

The fourth image data storage unit 69 stores the input compressed image frame data. The fourth image data storage unit 69 may be, for example, a detachable recording medium such as a memory card. The external interface unit 70 acquires the compressed image frame data from the fourth image data storage unit 69, converts the compressed image frame data into data suitable for protocol with the a peripheral device (not shown) of the display device 60, and outputs the compressed image frame data to the peripheral device (not shown).

Figure 7:
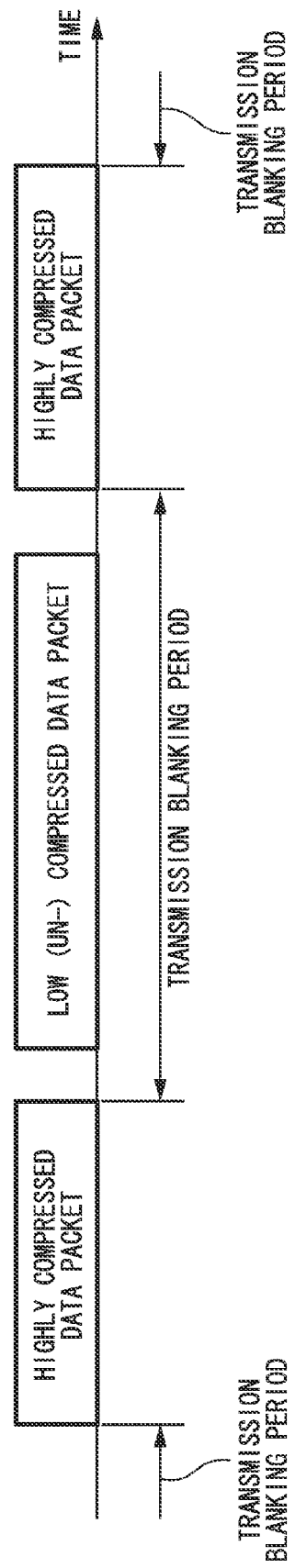
FIG. 7 is a diagram illustrating a packet data transmission time in a first wireless transmission unit 50 and a packet data transmission time in a second wireless transmission unit 53.

FIG. 7 is a diagram illustrating a packet data transmission time in the first wireless transmission unit 50 and a packet data transmission time in the second wireless transmission unit 53. The first wireless transmission unit 50 transmits a highly compressed data packet (e.g., moving image data). The second wireless transmission unit 53 transmits a low (un-) compressed data packet (e.g., still image data). Here, the endoscope control unit 43 may determine a transmission blanking period that is a period in which the first wireless transmission unit 50 does not transmit packet data, for example, according to whether all image frame data transmission has been completed or according to the packet data being transmitted in a given period. Further, the first wireless transmission unit 50 and the second wireless transmission unit 53 may alternately transmit packet data in a given period without depending on an instruction from the endoscope control unit 43.

Figure 8:
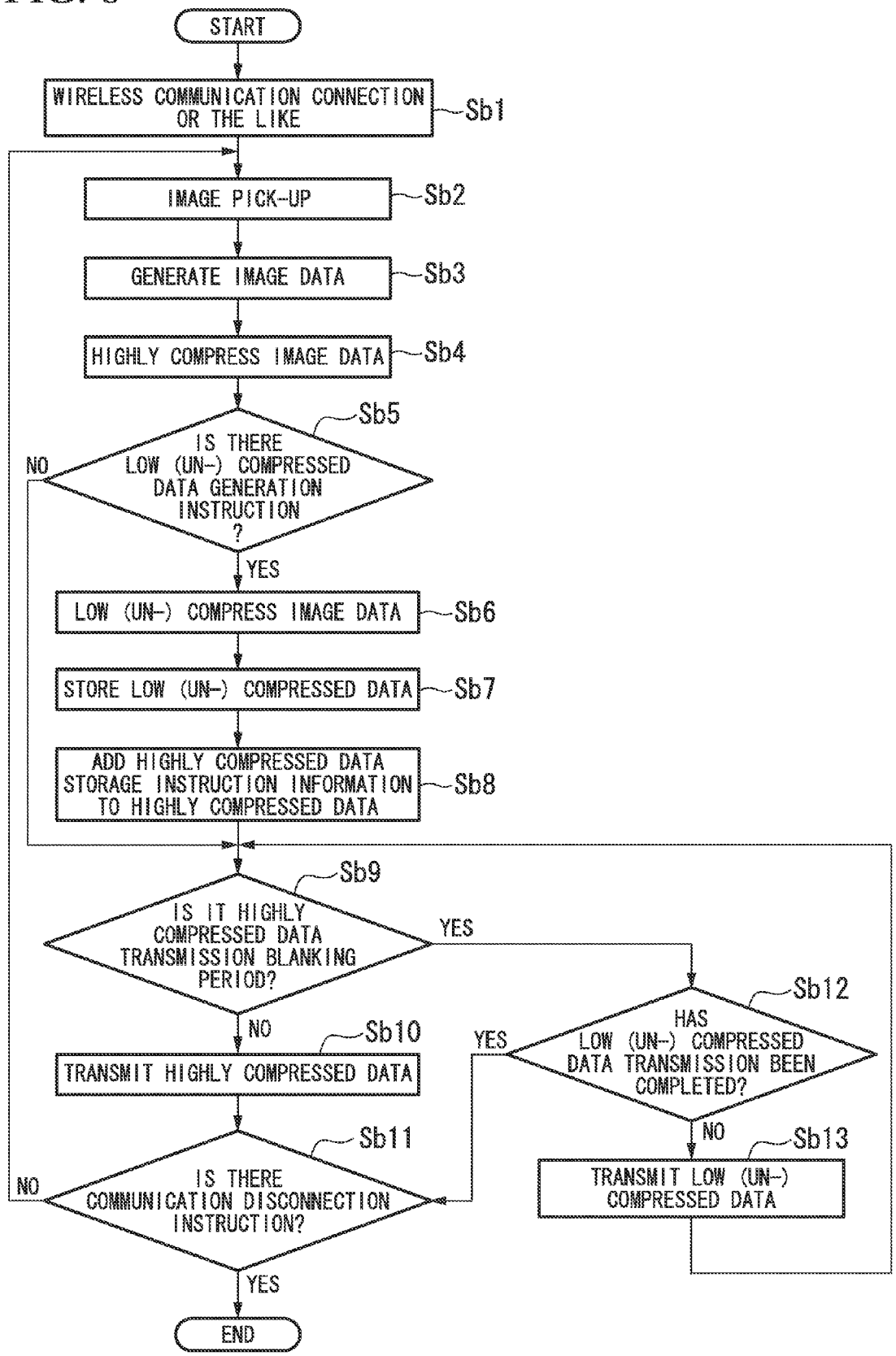
FIG. 8 is a flowchart illustrating operation of the endoscope in accordance with the second preferred embodiment of the present invention.

FIG. 8 is a flowchart illustrating operation of the endoscope in accordance with the second preferred embodiment of the present invention. The endoscope manipulation unit 41 receives a manipulation input from a surgeon, and outputs a manipulation signal to the endoscope control unit 43 and the endoscope power supply unit 42. The endoscope power supply unit 42 receives a communication connection instruction as the manipulation signal from the endoscope manipulation unit 41, and initiates power supply to each block of the endoscope 40.

The endoscope control unit 43 receives emission amount data for light irradiated into a coelom as a manipulation signal from the endoscope manipulation unit 41, and outputs the emission amount data to the light control unit 44. The light control unit 44 drives the light source unit 45 based on the emission amount data input from the endoscope control unit. The light source unit 45 supplies light to the light emitting unit 46, for example, via an optical fiber as driven by the light control unit 44. The light emitting unit 46 irradiates the supplied light into the coelom.

The endoscope control unit 43 receives a communication connection instruction as the manipulation signal from the endoscope manipulation unit 41. The endoscope control unit 43 outputs an instruction for a communication connection with the first wireless reception unit 64 of the display device 60 to the first wireless transmission unit 50. The first wireless transmission unit 50 receives the communication connection instruction from the endoscope control unit, and initiates packet communication with the first wireless reception unit 64 of the display device 60. Similarly, the second wireless transmission unit 53 initiates packet communication with the second wireless reception unit 68 of the display device 60 (step Sb1).

Steps Sb2 and Sb3 are the same as steps S2 and S3 in FIG. 3, respectively. The first image data compression unit 49 outputs the intra-frame-compressed image frame data to the first wireless transmission unit 50 (step Sb4).

The endoscope control unit 43 determines whether the endoscope control unit 43 receives a low (un-) compressed data generation instruction from the endoscope manipulation unit 41 (step Sb5). If the endoscope control unit 43 receives the low (un-) compressed data generation instruction (e.g., a still-image acquisition instruction) as a manipulation signal from the endoscope manipulation unit 41, the endoscope control unit 43 outputs a low (un-) compressed data generation instruction to the second image data compression unit 51. Further, the endoscope control unit 43 instructs the first wireless transmission unit 50 to add "highly compressed data storage instruction information" to the image frame data (highly compressed data) output by the first image data compression unit 49. If the endoscope control unit 43 does not receive the low (un-) compressed data generation instruction as the manipulation signal from the endoscope manipulation unit 41, the endoscope control unit 43 proceeds to step Sb9.

the second image data compression unit 51 receives the low (un-) compressed data generation instruction, the second image data compression unit 51 outputs the compressed image frame data to the third image data storage unit 52 (step Sb6). The third image data storage unit 52 receives and stores the compressed image frame data from the second image data compression unit 51 (step Sb7). The first wireless transmission unit 50 instructed to add the "highly compressed data storage instruction information" adds the "highly compressed data storage instruction information" to the highly compressed data (step Sb8).

Then, the endoscope control unit 43 determines whether a period is a transmission blanking period according to the above-described condition (step Sb9). If it is not a transmission blanking period, the endoscope control unit 43 instructs the first wireless transmission unit 50 to transmit packet data. The first wireless transmission unit 50 transmits packet data of image frame data (highly compressed data) as a wireless signal to the first wireless reception unit 64 of the display device 60 (step Sb10).

If the first wireless transmission unit 50 or the second wireless transmission unit 53 receives the communication disconnection instruction, the first wireless transmission unit 50 or the second wireless transmission unit 53 terminates the packet communication with the wireless reception unit of the display device 60. On the other hand, if the first wireless transmission unit 50 or the second wireless transmission unit 53 does not receive the communication disconnection instruction, the first wireless transmission unit 50 or the second wireless transmission unit 53 returns to step Sb2. Further, the endoscope power supply unit 42 determines whether the endoscope power supply unit 42 receives the communication disconnection instruction as the manipulation signal from the endoscope manipulation unit 41. If the endoscope power supply unit 42 receives the communication disconnection instruction, the endoscope power supply unit 42 stops the power supply to each block of the endoscope 40 after a given amount of time has elapsed. If the endoscope power supply unit 42 does not receive the communication disconnection instruction, the endoscope power supply unit 42 returns to step Sb2 (step Sb11).

If it is a transmission blanking period in step Sb9, the endoscope control unit 43 determines whether the packet data transmission in the second wireless transmission unit 53 has been previously completed. If the transmission has been completed, the endoscope control unit 43 proceeds to step Sb11 (step Sb12). If the transmission has not been completed, the endoscope control unit 43 instructs the second wireless transmission unit 53 to transmit the packet data. The second wireless transmission unit 53 transmits packet data of image frame data (low (un-) compressed data) as a wireless signal to the second wireless reception unit 68 of the display device 60, and proceeds to step Sb9 (step Sb13).

Figure 9:
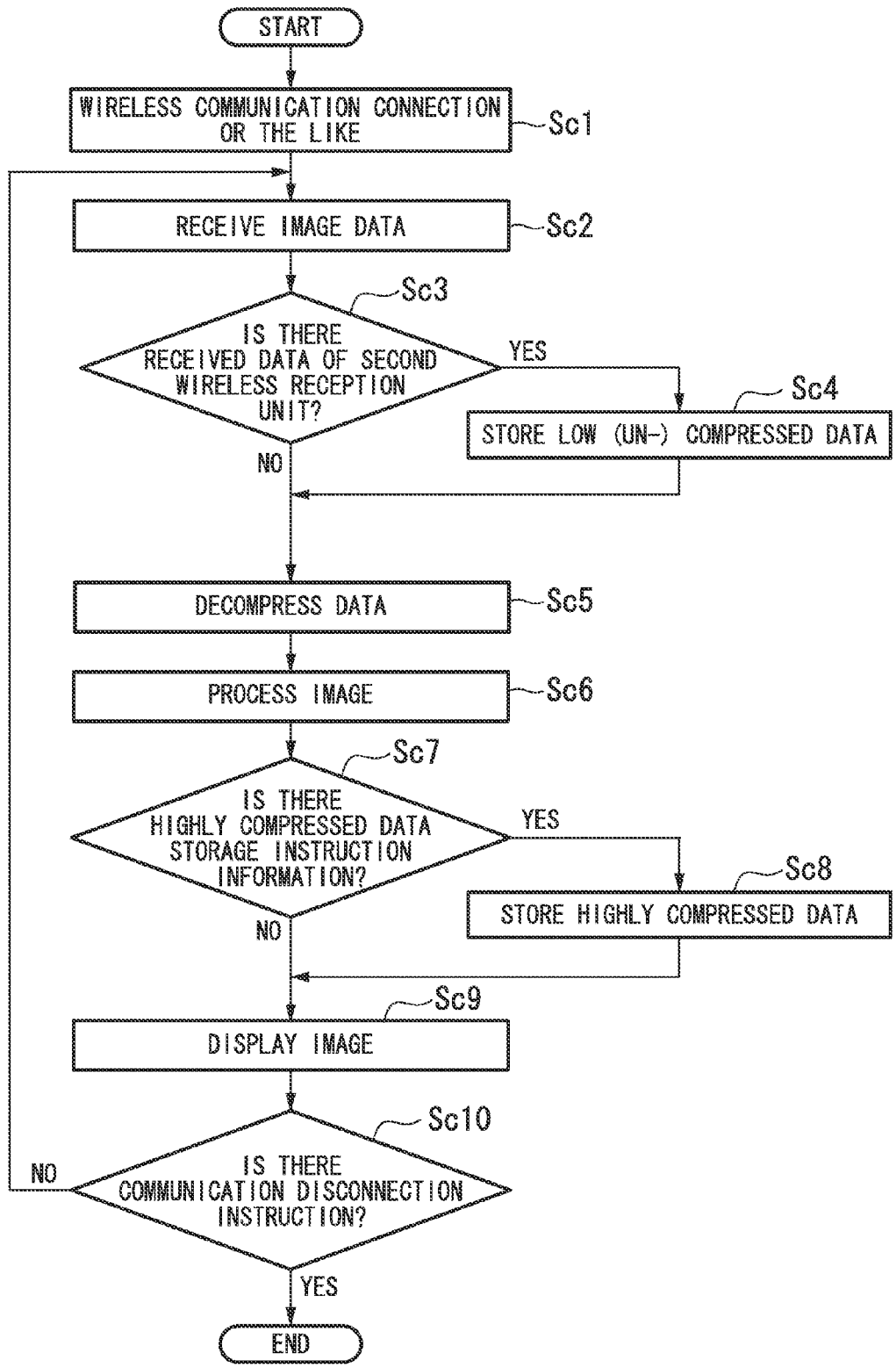
FIG. 9 is a flowchart illustrating operation of the display device in accordance with the second preferred embodiment of the present invention.

FIG. 9 is a flowchart illustrating operation of the display device in accordance with the second preferred embodiment of the present invention. The display device manipulation unit 61 receives a manipulation input from a surgeon, and outputs a manipulation signal to the display device control unit 63 and the display device power supply unit 62. The display device power supply unit 62 receives a communication connection instruction as the manipulation signal from the display device manipulation unit 61, and initiates power supply to each block of the display device 30.

The display device control unit 63 receives a communication connection instruction as the manipulation signal from the display device manipulation unit 61, and outputs an instruction for a communication connection with the first wireless transmission unit 50 of the endoscope 40 to the first wireless reception unit 64. The first wireless reception unit 64 receives the communication connection instruction from the display device control unit 63, and initiates packet communication with the first wireless transmission unit 50 of the endoscope 40. Similarly, the second wireless reception unit 68 receives the communication connection instruction from the display device control unit 63, and initiates packet communication with the second wireless transmission unit 53 of the endoscope 40 (step Sc1).

If the packet data is transmitted from the first wireless transmission unit 50, the first wireless reception unit 64 performs a demodulation process on the received packet data to acquire the compressed image frame data from the packet data, and outputs the compressed image frame data to the image data decompression unit 65 (step Sc2). If the packet data is transmitted from the second wireless transmission unit 53, the second wireless reception unit 68 performs a demodulation process on the received packet data to acquire the compressed image frame data from the packet data, and outputs the compressed image frame data to the image data decompression unit 65 and the fourth image data storage unit

69. The fourth image data storage unit 69 stores the compressed image frame data (low (un-) compressed data) (step Sc4).

The image data decompression unit 65 performs a decompression process using a plurality of packet data. Accordingly, even when the packet data is not received in step Sc2, the image data decompression unit 65 performs the decompression process on the previously input compressed image frame data (step Sc5). The image processing unit 66 performs image processing on the decompressed image frame data, and outputs the processed image frame data to the display unit 67 (step Sc6).

The first wireless reception unit 64 determines whether the "highly compressed data storage instruction information" has been added to the image frame data of the received packet data (step Sc7). If the "highly compressed data storage instruction information" has been added, the first wireless reception unit 64 outputs the compressed image frame data to the fourth image data storage unit 69. The fourth image data storage unit 69 stores the compressed image frame data (step Sc8).

The display unit 67 displays the processed image frame data as an image, for example, on a display (step Sc9). If the first wireless reception unit 64 or the second wireless reception unit 68 receives the communication disconnection instruction, the first wireless reception unit 64 or the second wireless reception unit 68 terminates packet communication with each wireless transmission unit of the endoscope 40. On the other hand, if the first wireless reception unit 64 or the second wireless reception unit 68 does not receive the communication disconnection instruction, the first wireless reception unit 64 or the second wireless reception unit 68 returns to step Sc2. Further, the display device power supply unit 62 determines whether the communication disconnection instruction is received from the display device manipulation unit 61 as a manipulation signal. If the communication disconnection instruction is received, the display device power supply unit 62 stops the power supply to each block of the display device 60 after a given amount of time has elapsed. If the communication disconnection instruction is not received, the display device power supply unit 62 returns to step Sc2 (step Sc10).

Thus, since the second wireless transmission unit 53 of the endoscope 40 wirelessly transmits the low (un-) compressed data (e.g., still image data) having a large data size in the transmission blanking period of the highly compressed data (e.g., moving image data), the first wireless transmission unit 50 can wirelessly transmit the highly compressed data to the display device 60 without decreasing a communication speed. Accordingly, the surgeon can obtain high-definition still image data from the fourth image data storage unit 69 of the display device 60 and the external interface unit 70.

Figure 10:
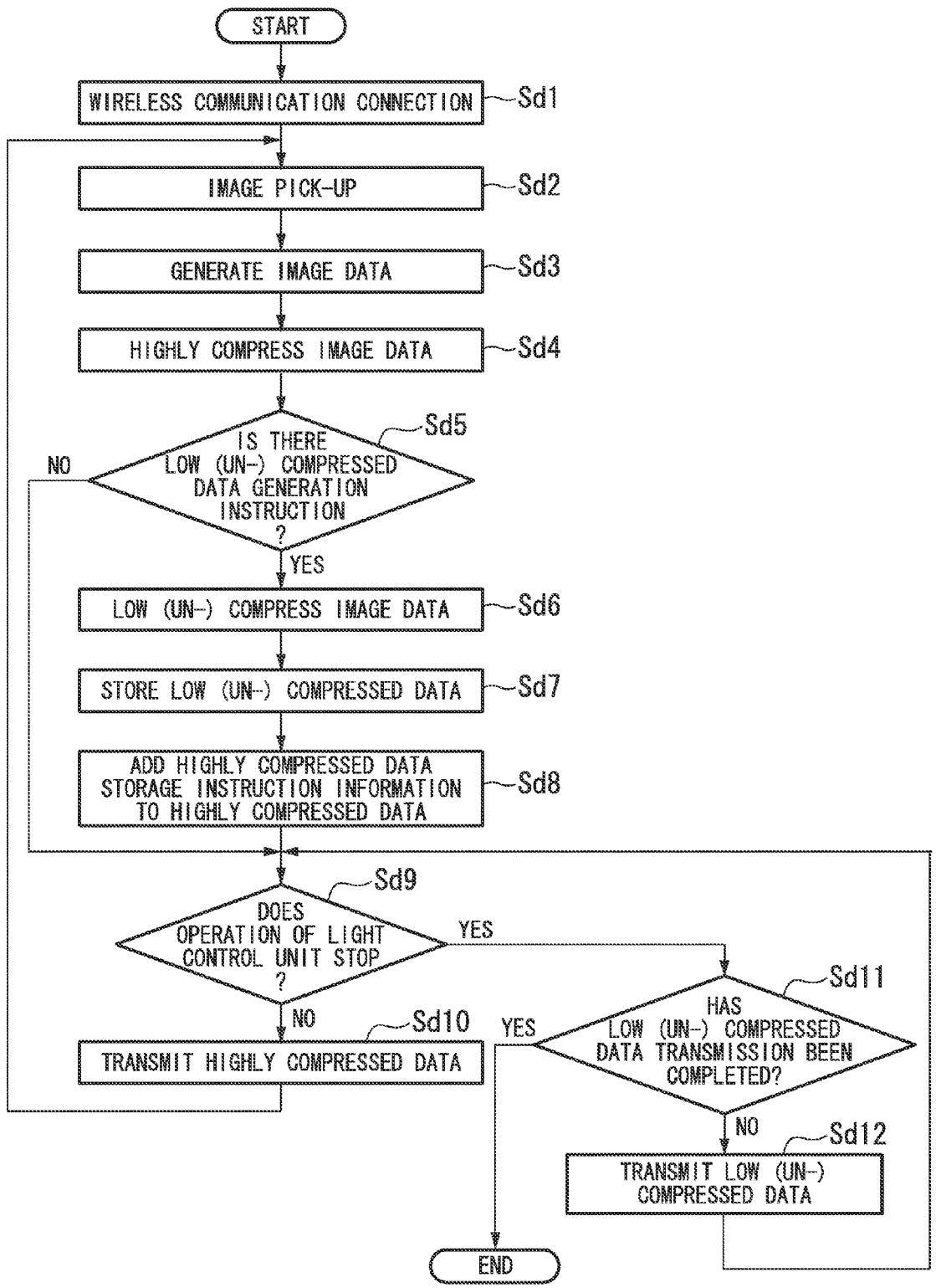
FIG. 10 is a flowchart illustrating operation of the endoscope in accordance with the second preferred embodiment of the present invention.

A transmission time of the low (un-) compressed data (e.g., still image data) may be determined as follows. FIG. 10 is a flowchart illustrating operation of the endoscope in accordance with the second preferred embodiment of the present invention. Here, steps Sd1 to Sd8 are the same as steps Sb1 to Sb8 in FIG. 8.

If the surgeon terminates examination using the endoscope 40, the endoscope manipulation unit 41 receives an instruction to stop the light control unit 44 (an instruction to turn the light emitting unit 46 off), and notifies the endoscope control unit 43 of the instruction to stop the light control unit 44. The endoscope control unit 43 determines whether the endoscope control unit 43 receives the instruction to stop the light control unit 44 from the endoscope manipulation unit 41 (step Sd9). If the endoscope control unit 43 does not receive the instruction to stop the light control unit 44, it is assumed that the surgeon continues to perform the examination using the endoscope 40, and accordingly, the endoscope control unit 43 instructs the first wireless transmission unit 50 to transmit the packet data of the image frame data (highly compressed data). The first wireless transmission unit 50 transmits the packet data of the image frame data (highly compressed data) as a wireless signal to the first wireless reception unit 64 of the display device 60, and proceeds to step Sd2 (step Sd10).

If the endoscope control unit 43 receives an instruction to stop the light control unit 44, it is assumed that the surgeon terminates the examination using the endoscope 40. Accordingly, the endoscope control unit 43 receives the instruction to stop the light control unit 44 and stops the operation of the light control unit 44. Further, the endoscope control unit 43 instructs the first wireless transmission unit 50 to stop the transmission of the image frame data. Further, the endoscope control unit 43 determines whether batch transmission of the packet data in the second wireless transmission unit 53 has been completed. If the transmission has not been completed, the endoscope control unit 43 instructs the second wireless transmission unit 53 to transmit non-transmitted packet data. The second wireless transmission unit 53 having received the packet data transmission instruction transmits the packet data of image frame data (low (un-) compressed data) as a wireless signal to the second wireless reception unit 68 of the display device 60, and proceeds to step Sd9 (step Sd12).

Thus, since the second wireless transmission unit 53 of the endoscope 40 wirelessly batch-transmits the low (un-) compressed data (e.g., still image data) having a large data size after the transmission of the highly compressed data (e.g., moving image data) stops, the first wireless transmission unit 50 can wirelessly transmit the highly compressed data to the display device 60 without decreasing a communication speed. Accordingly, the surgeon can obtain high-definition still image data from the fourth image data storage unit 69 of the display device 60 and the external interface unit 70.

Further, a determination condition in step Sd9 of FIG. 10 may be whether the communication disconnection instruction to the endoscope power supply unit 42, i.e., the power supply stop instruction to the endoscope 40, is received, not whether the instruction to stop the light control unit 44 is received. Further, if power held in the endoscope power supply unit 42 is not sufficient, the endoscope 40 may wait for the endoscope power supply unit 42 to be charged and batch-transmit the packet data to the display device 60 using a next power supply instruction as a trigger.

Third Preferred Embodiment

Figure 11:
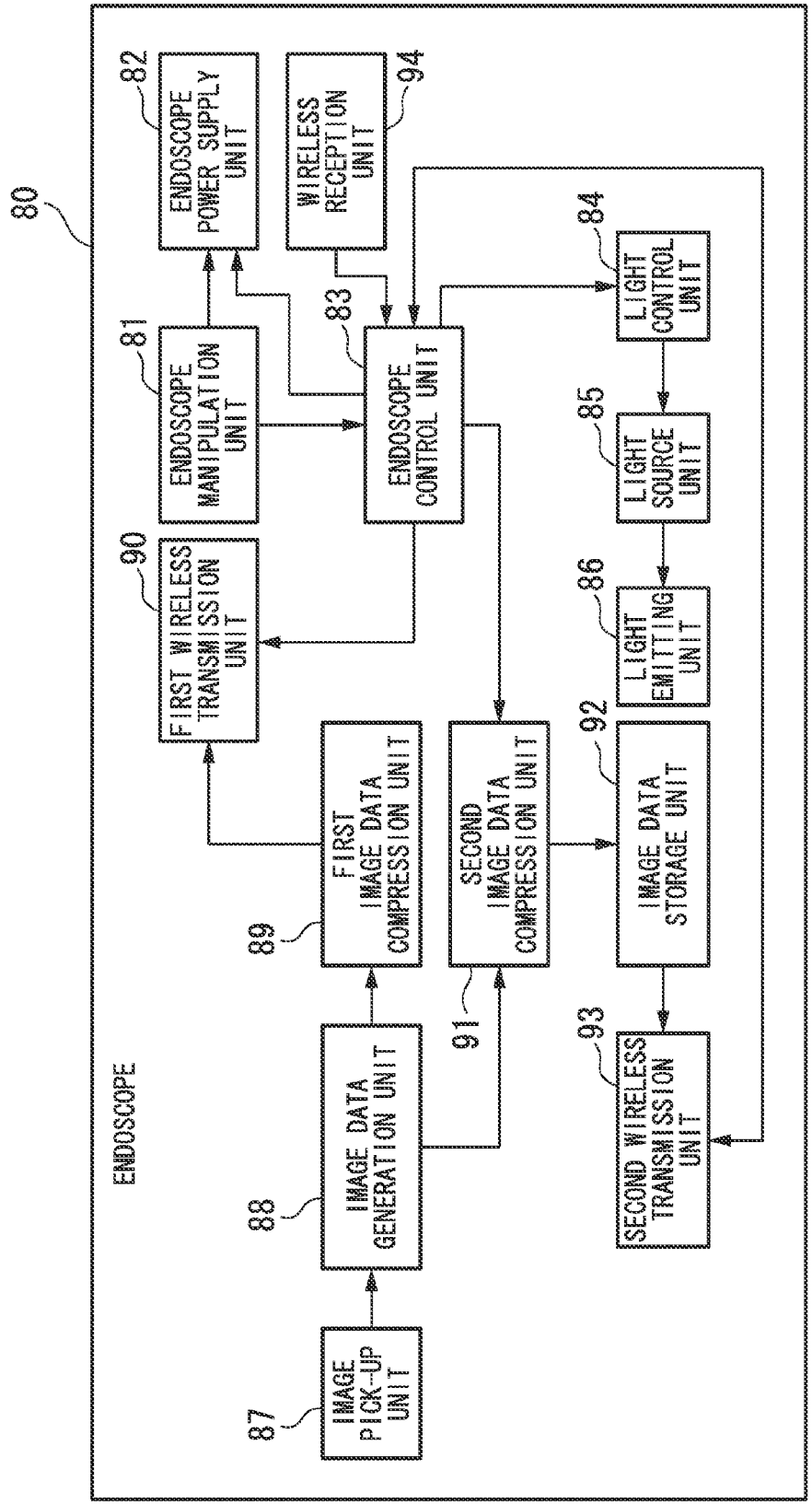
FIG. 11 is a block diagram illustrating an endoscope in accordance with a third preferred embodiment of the present invention.

Next, a third preferred embodiment of the present invention will be described. FIG. 11 is a block diagram illustrating an endoscope in accordance with the third preferred embodiment of the present invention. In FIG. 11, an endoscope 80 (image transmission apparatus) includes an endoscope manipulation unit 81, an endoscope power supply unit 82 (power supply unit), an endoscope control unit 83 (control unit), a light control unit 84, a light source unit 85, a light emitting unit 86, an image pickup unit 87, an image data generation unit 88, a first image data compression unit 89, a first wireless transmission unit 90, a second image data compression unit 91, an image data storage unit 92, a second wireless transmission unit 93, and a wireless reception unit 94.

In FIG. 11, the endoscope manipulation unit 81, the light control unit 84, the light source unit 85, the light emitting unit 86, the image pickup unit 87, the image data generation unit 88, the first image data compression unit 89, the first wireless transmission unit 90, the second image data compression unit 91, and the image data storage unit 92 perform the same operations as the endoscope manipulation unit 41, the light control unit 44, the light source unit 45, the light emitting unit 46, the image pickup unit 47, the image data generation unit 48, the first image data compression unit 49, the first wireless transmission unit 50, the second image data compression unit 51, and the third image data storage unit 52 in FIG. 5, respectively.

The endoscope power supply unit 82 performs the same operation as the endoscope power supply unit 42 in FIG. 5. In other words, the endoscope power supply unit 82 supplies power to the endoscope 80 (its own apparatus). However, the endoscope power supply unit 82 receives a communication disconnection instruction from the endoscope control unit 83, not from the endoscope manipulation unit 81. The endoscope control unit 83 performs the same operation as the endoscope control unit 43 in FIG. 5. However, if the communication disconnection instruction is received from the endoscope manipulation unit 81 or reception information of the communication disconnection signal is received from the wireless reception unit 94 and if reception information of a reception completion signal is received from the wireless reception unit 94, the endoscope control unit 83 outputs the communication disconnection instruction to the first wireless transmission unit 90, the second wireless transmission unit 93, the wireless reception unit 94, and the endoscope power supply unit 82. Alternatively, if the communication disconnection instruction is received from the endoscope manipulation unit 81 or reception information of the communication disconnection signal is received from the wireless reception unit 94, the endoscope control unit 83 may instruct the first wireless transmission unit 90 to output the communication disconnection instruction irrespective of whether the wireless reception unit 94 receives the reception completion signal.

Further, the endoscope power supply unit 82 may stop the power supply in response to a power-off instruction rather than the communication disconnection instruction. In this case, the endoscope manipulation unit 81 receives a manipulation of a power-off instruction rather than the communication disconnection instruction. If the endoscope control unit 83 receives the power-off instruction after outputting the communication disconnection instruction, for example, to the second wireless transmission unit 93, the endoscope control unit 83 immediately outputs a power-off instruction (the above-described communication disconnection instruction) to the endoscope power supply unit 82. If the endoscope control unit 83 receives the power-off instruction before outputting the communication disconnection instruction, the endoscope control unit 83 outputs the power-off instruction to the endoscope power supply unit 82 when outputting the communication disconnection instruction, for example, to the second wireless transmission unit 93. Accordingly, it is possible to prevent the endoscope power supply unit 82 from stopping the power supply before the communication is completed.

As described above, the first image data compression unit 89 intra-frame compresses the image frame data at a high compression rate (lossy compression) and continuously transmits the compressed image frame data as moving image data to the first wireless transmission unit 90, similar to the first image data compression unit 49 in FIG. 5.

The first wireless transmission unit 90 performs the same operation as the first wireless transmission unit 50 in FIG. 5. In other words, as described about the first wireless transmission unit 20 of FIG. 1, the first wireless transmission unit 90 performs a modulation process on the lossy-compressed image frame data input from the first image data compression unit 89 and transmits packet data of the modulated image frame data (the moving image compressed by the lossy compression) as first image data to a first wireless reception unit 104 of a display device 100 (external apparatus) shown in FIG. 12, which will be described later, through wireless communication.

The second wireless transmission unit 93 performs the same operation as the second wireless transmission unit 53 in FIG. 5. In addition, the second wireless transmission unit 93 transmits a first communication disconnection signal in response to an instruction from the endoscope control unit 83. Here, the first communication disconnection signal is a signal indicating that the communication disconnection instruction is output from the endoscope manipulation unit 81 to the endoscope manipulation unit 83. The second wireless transmission unit 93 transmits the communication disconnection signal to a second wireless reception unit 108 of the display device 100 shown in FIG. 12, which will be described later, using a dedicated packet whose format is known to the second wireless reception unit 108. Further, information indicating the communication disconnection signal may be contained in a head of the packet for transmitting the low (un-) compressed data, so that the second wireless transmission unit 93 can transmit the signal. In this case, when there is no low (un-) compressed data to be transmitted, the second wireless transmission unit 93 includes the information indicating the communication disconnection signal in a header of a packet of empty data and transmits the packet.

Figure 12:
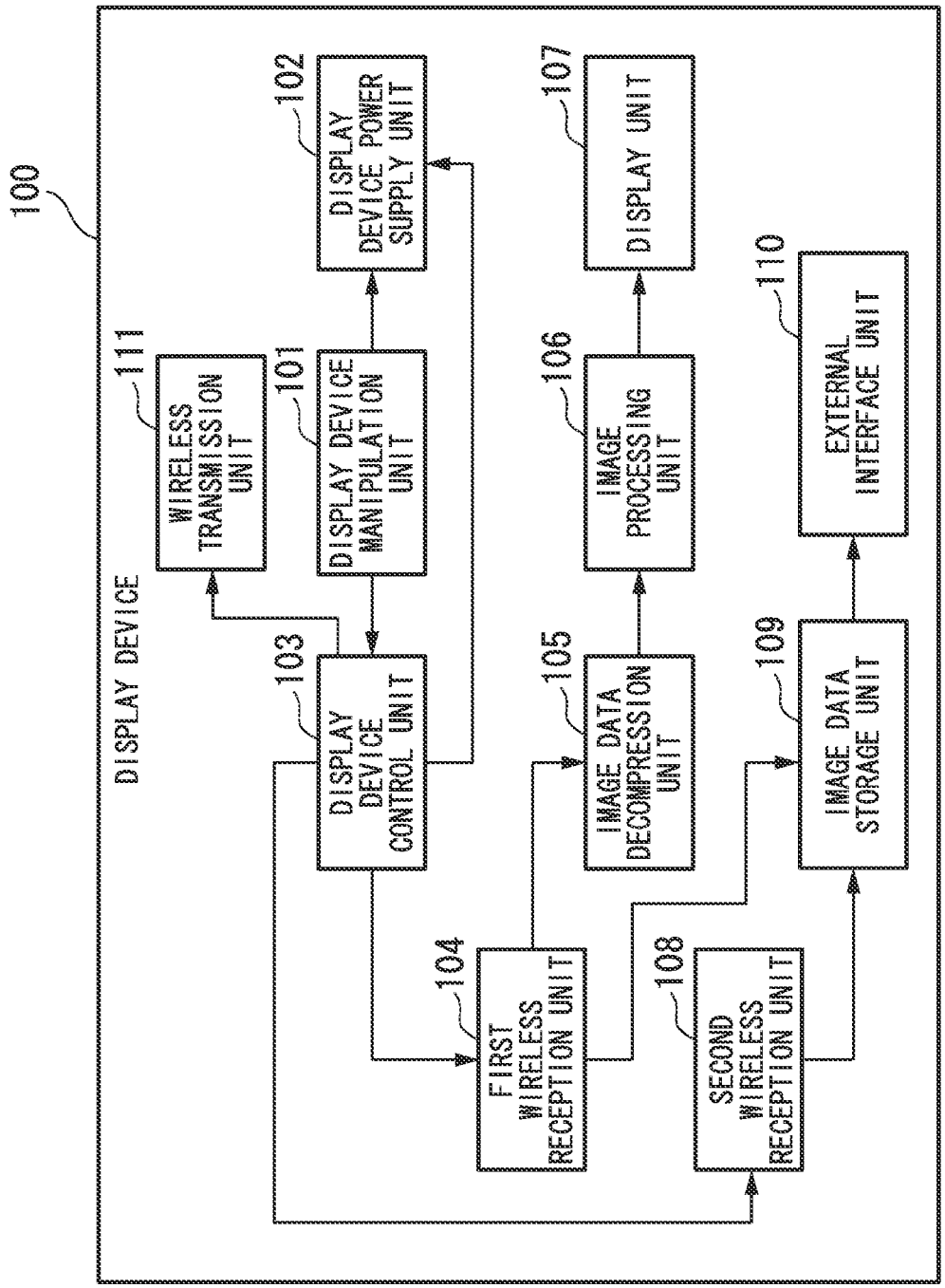
FIG. 12 is a block diagram illustrating a display device 100 in accordance with the third preferred embodiment of the present invention.

As described about the second image data compression unit 51 of FIG. 5, the second image data compression unit 91 outputs image frame data (image data corresponding to one image in the moving image) as second image data that is image data compressed at a lower compression rate than the lossy compression or not compressed, to the image data storage unit 92, and the second wireless transmission unit 93 transmits this image data to the second wireless reception unit 108 of the display device 100 shown in FIG. 12. Accordingly, the second wireless transmission unit 93, together with the first wireless transmission unit 90 (both corresponding to a transmission unit), transmits the moving image compressed by the lossy compression as first image data to an external apparatus through wireless communication, and transmits the image data corresponding to one image in the moving image as second image data that is image data compressed at a lower compression rate than the lossy compression or not compressed. Here, a ratio B/A of a size B of the compressed data to a size A of original data is defined as a compression rate. A small value of the compression rate is defined as a high compression rate, and a large value of the compression rate is defined as a low compression rate.

The wireless reception unit 94 receives a second communication disconnection signal and a reception completion signal. If the wireless reception unit 94 receives one of the signals, the wireless reception unit 94 outputs reception information of the signal to the endoscope control unit 83. Further, if the wireless reception unit 94 receives the communication disconnection instruction from the endoscope control unit 83, the wireless reception unit 94 disconnects the communication.

FIG. 12 is a block diagram illustrating the display device 100 (image reception apparatus) in accordance with the third preferred embodiment of the present invention. In FIG. 12, the display device 100 includes a display device manipulation unit 101, a display device power supply unit 102, a display device control unit 103, the first wireless reception unit 104, an image data decompression unit 105, an image processing unit 106, a display unit 107, the second wireless reception unit 108, an image data storage unit 109, an external interface unit 110, and a wireless transmission unit 111.

In FIG. 12, the display device manipulation unit 101, the first wireless reception unit 104, the image data decompression unit 105, the image processing unit 106, the display unit 107, the image data storage unit 109, and the external interface unit 110 perform the same operations as the display device manipulation unit 61, the first wireless reception unit 64, the image data decompression unit 65, the image processing unit 66, the display unit 67, the fourth image data storage unit 69, and the external interface unit 70 in FIG. 6, respectively. Since the first wireless reception unit 104 receives a signal from the first wireless transmission unit 90 in FIG. 11 and the second wireless reception unit 108 receives a signal from the second wireless transmission unit 93 of FIG. 11, the second wireless reception unit 108, together with the first wireless reception unit 104 (both corresponding to a reception unit), receives the moving image compressed by the lossy compression as first image data from an external apparatus through wireless communication, and receives image data corresponding to one image in the moving image as second image data that is image data compressed at a lower compression rate than the lossy compression or not compressed.

The display device power supply unit 102 performs the same operation as the display device power supply unit 62 in FIG. 6. In other words, the display device power supply unit 102 (power supply unit) supplies power to the display device 100 (its own apparatus). However, the display device power supply unit 102 receives the communication disconnection instruction from the display device control unit 103, not from the display device manipulation unit 101, and causes the display device 100 to enter a standby state. The display device control unit 103 performs the same operation as the display device control unit 63 in FIG. 6. However, the display device control unit 103 receives, from the second wireless reception unit 108, information indicating whether the second wireless reception unit 108 has completed the reception of the image data from the second wireless transmission unit 93 of the endoscope 80. Further, if the communication disconnection instruction is received from the display device control unit 101 or reception information of the communication disconnection signal is received from the second wireless reception unit 108 and if the reception completion information is received from the second wireless reception unit 108, the display device control unit 103 outputs the communication disconnection instruction to the first wireless reception unit 104, the second wireless reception unit 108, the wireless transmission unit 111, and the display device power supply unit 102. Further, if the display device control unit 103 receives the communication disconnection instruction from the display device manipulation unit 101 or receives the reception information of the communication disconnection signal from the second wireless reception unit 108, the display device control unit 103 may output the communication disconnection instruction to the first wireless reception unit 108 irrespective of whether the display device control unit 103 receives the reception completion information from the second wireless reception unit 108.

The second wireless reception unit 108 performs the same operation as the second wireless reception unit 68 in FIG. 6. In addition, the second wireless reception unit 108 receives the first communication disconnection signal from the second wireless transmission unit 93 of the endoscope 80 shown in FIG. 11.

The wireless transmission unit 111 transmits the second communication disconnection signal and the reception completion signal to the wireless reception unit 94 of the endoscope 80 in response to an instruction of the display device control unit 103. Here, the second communication disconnection signal is a signal indicating that the display device manipulation unit 101 receives a communication disconnection instruction from the user. The reception completion signal is a signal indicating that the second wireless reception unit 108 has completed the reception of the packet data. Since the display device 100 determines that packet data transmission in the second wireless transmission unit 93 of the endoscope 80 has been completed and transmits the reception completion signal, the reception completion signal is also a signal indicating that the second wireless transmission unit 93 of FIG. 11 has completed the transmission. If the wireless transmission unit 111 receives the communication disconnection instruction from the display device control unit 103, the wireless transmission unit 111 disconnects the communication from the wireless reception unit 94 of the endoscope 80.

Figure 13:
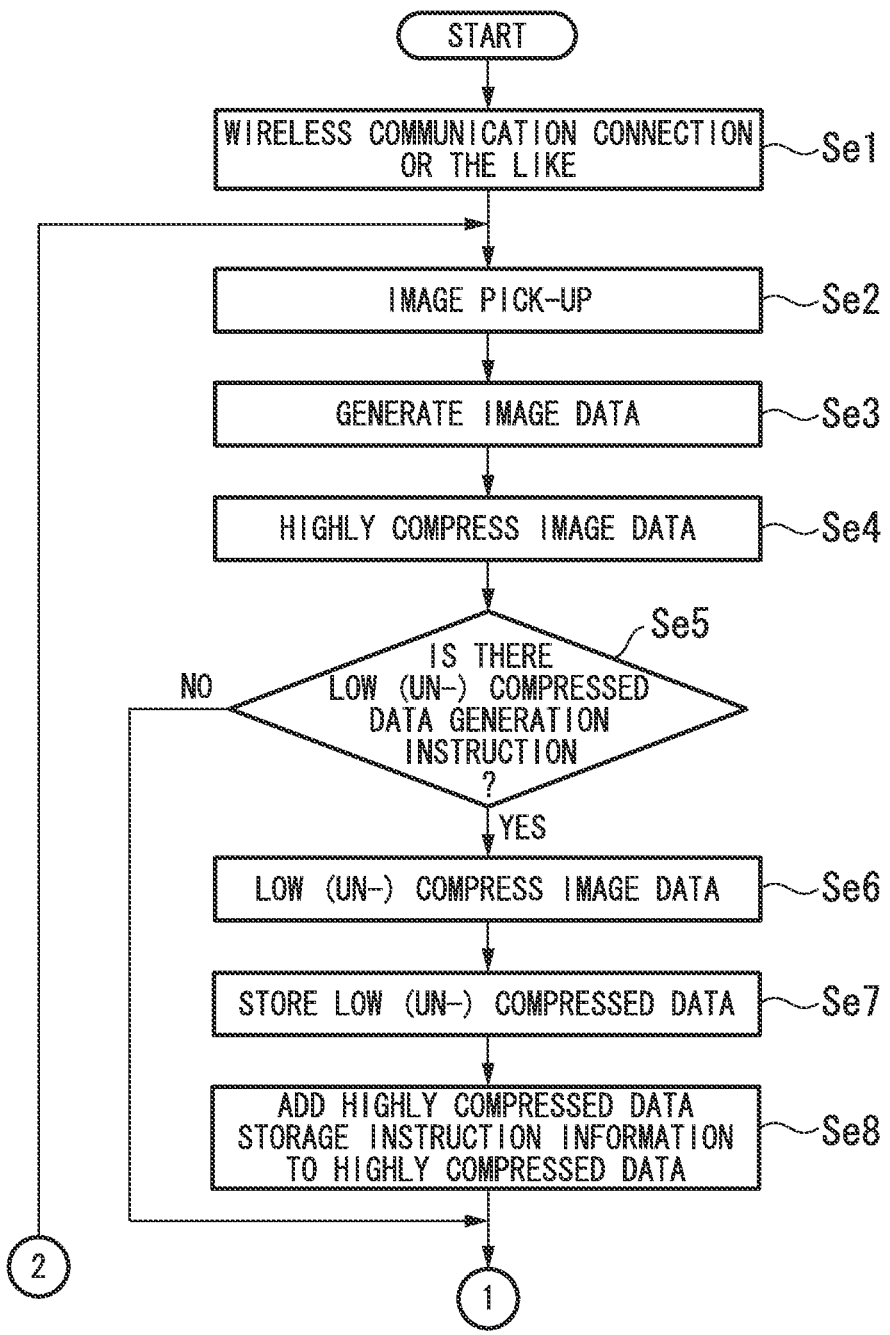
FIGS. 13 and 14 are flowcharts illustrating operation of the endoscope 80 in accordance with the third preferred embodiment of the present invention.
Figure 14:
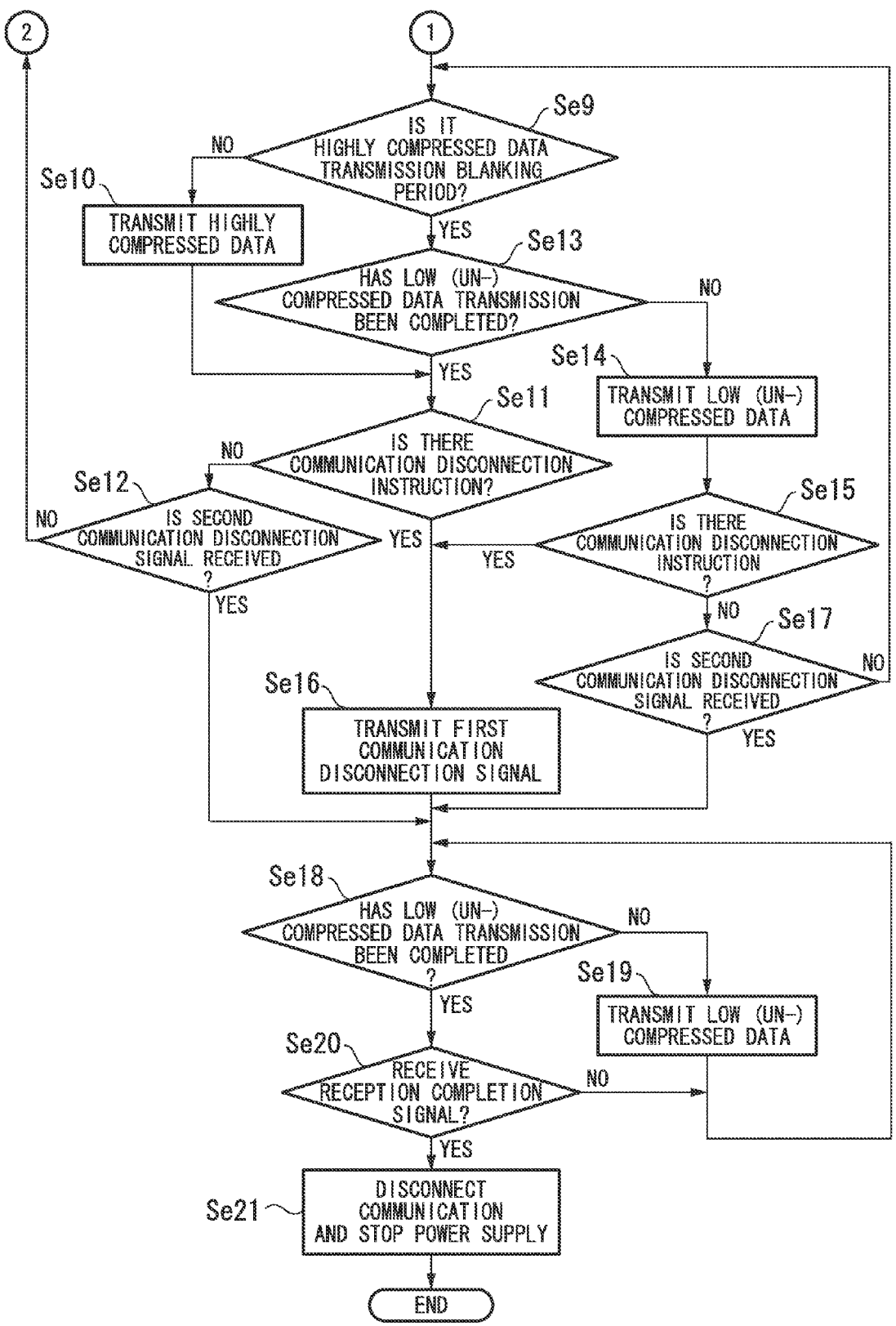

FIGS. 13 and 14 are flowcharts illustrating operation of the endoscope 80 in accordance with the third preferred embodiment of the present invention. Steps Se1 to Se8 in FIG. 13 are the same as steps Sb1 to Sb8 in FIG. 8. If the endoscope control unit 83 does not receive a low (un-) compressed data generation instruction from the endoscope manipulation unit 81 in step Se5 of FIG. 13 and if step Se8 in FIG. 8 ends, the endoscope control unit 83 proceeds to step Se9 in FIG. 14. The endoscope control unit 83 determines whether a period is a transmission blanking period described in FIG. 7 (step Se9). If it is not a transmission blanking period, the endoscope control unit 83 instructs the first wireless transmission unit 90 to transmit the packet data, and the first wireless transmission unit 90 transmits the packet data of image frame data (highly compressed data) as a wireless signal to the first wireless reception unit 104 of the display device 100 (step Se 10).

The endoscope control unit 83 determines whether the communication disconnection instruction is received from the endoscope manipulation unit 81 (step Se11). If the communication disconnection instruction has not been received, the endoscope control unit 83 determines whether reception information of the second communication disconnection signal is received from the wireless reception unit 94 (step Se12). If the reception information has not been received, the endoscope control unit 83 returns to step Set in FIG. 13. If the communication disconnection instruction has been received in step Se11, the endoscope control unit 83 proceeds to step Se16, which will be described later. If the reception information of the second communication disconnection signal has been received in step Se12, the endoscope control unit 83 proceeds to step Se18, which will be described later.

If it is a transmission blanking period in step Se9, the endoscope control unit 83 determines whether the packet data transmission of the second wireless transmission unit 93 has been previously completed (step Se13). If the transmission has been completed, the endoscope control unit 83 proceeds to step Se11. If the transmission has not been completed, the endoscope control unit 83 instructs the second wireless transmission unit 93 to transmit the packet data. The second wireless transmission unit 93 transmits packet data of image frame data (low (un-) compressed data) to the second wireless reception unit 108 of the display device 100 (step Se14).

The endoscope control unit 83 determines whether the communication disconnection instruction has been received from the endoscope manipulation unit 81 (step Se15). If the communication disconnection instruction has not been received, the endoscope control unit 83 determines whether the reception information of the second communication disconnection signal has been received from the wireless reception unit 94 (step Se17). If the second communication disconnection signal has not been received, the endoscope control unit 83 returns to step Se9.

If the communication disconnection instruction has been received from the endoscope manipulation unit 81 in step Se11 and if the communication disconnection instruction has been received from the endoscope manipulation unit 81 in step Se15, the endoscope control unit 83 instructs the second wireless transmission unit 93 to transmit the first communication disconnection signal, and the second wireless transmission unit 93 transmits the first communication disconnection signal to the second wireless reception unit 108 of the display device 100 (step Se 16).

After step Se 16 ends, if the reception information of the second communication disconnection signal has been received in step Se12, and if the reception information of the second communication disconnection signal has been received in step Se 17, the endoscope control unit 83 determines whether packet data transmission of the second wireless transmission unit 93 has been previously completed (step Se 18). If the transmission has not been completed, the endoscope control unit 83 instructs the second wireless transmission unit 93 to transmit the packet data, and the second wireless transmission unit 93 transmits packet data of image frame data (low (un-) compressed data) to the second wireless reception unit 108 of the display device 100 (step Se19).

If the transmission has been completed in step Se 18, the endoscope control unit 83 determines whether reception information of a reception completion signal has been received from the wireless reception unit 94 (step Se20). If the reception information of the reception completion signal has been received, the endoscope control unit 83 outputs an instruction for a communication disconnection from the first wireless reception unit 104 of the display device 100 to the first wireless transmission unit 90. The first wireless transmission unit 90 disconnects the communication. Further, the endoscope control unit 83 outputs an instruction for a communication disconnection from the second wireless reception unit 108 of the display device 100 to the second wireless transmission unit 93. The second wireless transmission unit 93 disconnects the communication. Further, the endoscope control unit 83 outputs an instruction for a communication disconnection from the wireless transmission unit 111 of the display device 100 to the wireless reception unit 94. The wireless reception unit 94 disconnects the communication. Further, the endoscope control unit 83 outputs a communication disconnection instruction to the endoscope power supply unit. The endoscope power supply unit 82 stops the power supply to each block (step Se21). Accordingly, the endoscope 80 ends the process.

Further, if the reception completion signal from the display device 100 has not been received despite the endoscope 80 having completed the packet data transmission in step Se18, the endoscope 80 performs the packet data retransmission, which is neither shown nor described.

The communication disconnection instruction output by the endoscope manipulation unit 81 in step Se11 or Se15 described above is a signal for disconnecting the wireless communication in response to an external user manipulation. Further, the second communication disconnection signal received by the wireless reception unit 94 in step Se12 or Se17 is a signal for disconnecting the wireless communication, which is transmitted by the display device 100 in response to an external user manipulation. In other words, the endoscope manipulation unit 81 and the wireless reception unit 94 correspond to an instructing unit for outputting a disconnection signal to disconnect the wireless communication in response to an external manipulation.

Further, after the endoscope control unit 83 (control unit) receives the communication disconnection instruction from the endoscope manipulation unit 81 or the second communication disconnection signal from the wireless reception unit 94 and receives the reception completion signal indicating that the second image data transmission in the second wireless transmission unit 93 has been completed from the wireless reception unit 94 in step Se20, the endoscope control unit 83 controls to disconnect the wireless communication in the first wireless transmission unit 90 and the second wireless transmission unit 93 and also controls to stop the power supply from the endoscope power supply unit 82 (step Se21).

Further, if the communication disconnection instruction from the endoscope manipulation unit 81 or the second communication disconnection signal from the wireless reception unit 94 is received during transmission of the first image data, the endoscope control unit 83 determines that the packet data transmission of the second wireless transmission unit 93 has been completed in step Se 18 and proceeds to step Se20. In this case, since the second wireless transmission unit 93 has completed the image data transmission, the second wireless reception unit 108 of the display device 100 has completed the reception of the image data. Accordingly, the wireless reception unit 94 receives the reception completion signal in step Se20, and the endoscope control unit 83 performs the above-described control of the communication disconnection in step Se21. In other words, if the endoscope control unit 83 receives the communication disconnection instruction from the endoscope manipulation unit 81 or the second communication disconnection signal from the wireless reception unit 94 during transmission of only the first image data, the endoscope control unit 83 immediately disconnects the wireless communication.

Figure 15:
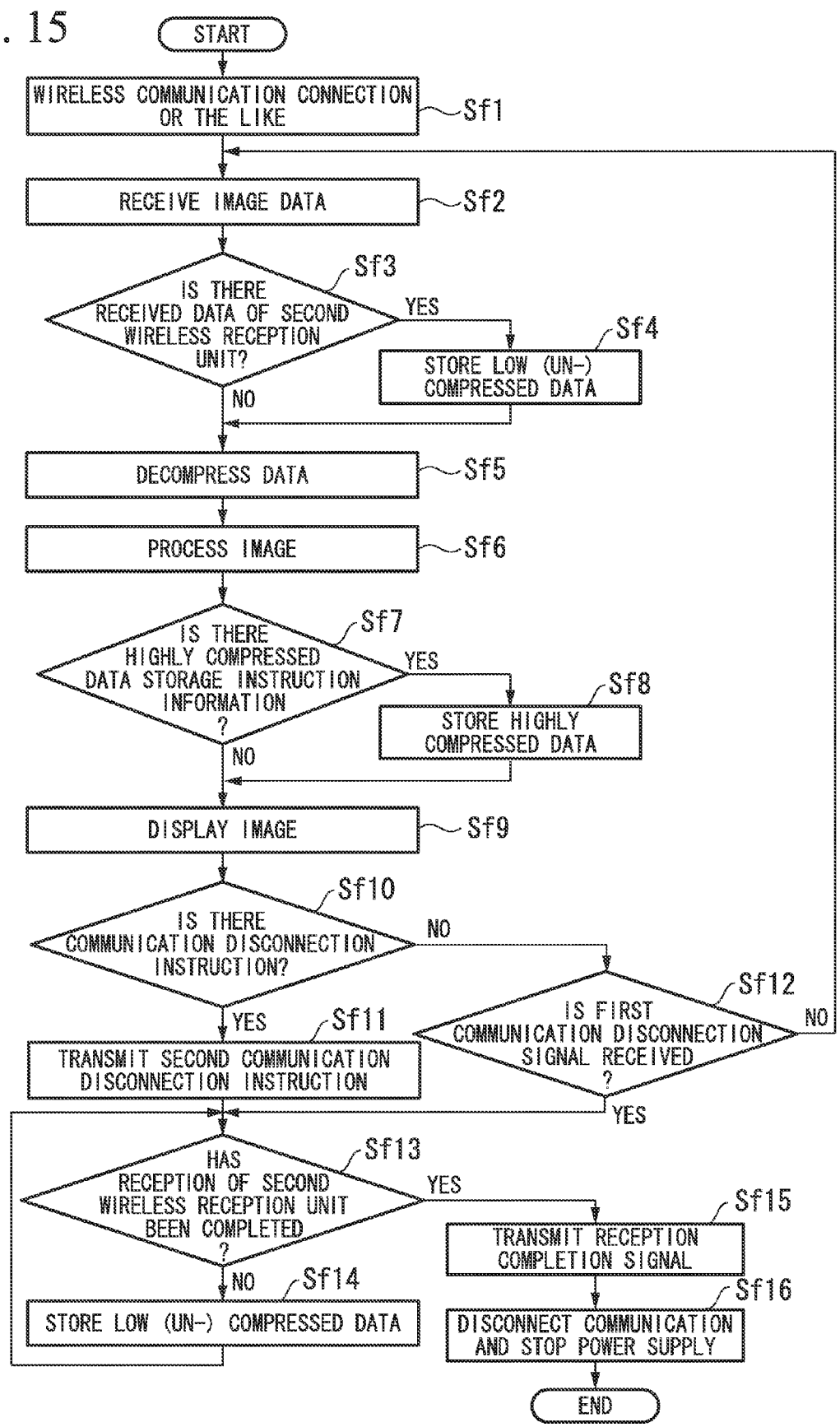
FIG. 15 is a flowchart illustrating operation of the display device 101 in accordance with the third preferred embodiment of the present invention.

FIG. 15 is a flowchart illustrating operation of the display device 100 in accordance with the third preferred embodiment of the present invention. Steps Sf1 and Sf2 of FIG. 15 are the same as steps Sc1 and Sc2 in FIG. 9. The display device control unit 103 determines whether there is packet data received by the second wireless reception unit 108 and not yet processed (step Sf3). If there is the packet data, the second wireless reception unit 108 receives the packet data, performs a demodulation process on the received packet data to acquire the compressed image frame data from the packet data, and outputs the compressed image frame data to the image data storage unit 109, and the image data storage unit 109 stores the compressed image frame data (low (un-) compressed data) (step Sf4).

If there is no unprocessed packet data in step Sf3 and if step Sf4 ends, the display device control unit 103 proceeds to step Sf5. Steps Sf5 to Sf9 are the same as steps Sc5 to Sc9 in FIG. 9. The display device control unit 103 determines whether the communication disconnection instruction has been received from the display device manipulation unit 101 (step Sf10). If the communication disconnection instruction has been received, the display device control unit 103 instructs the wireless transmission unit 111 to transmit the second communication disconnection signal. The wireless transmission unit 111 transmits the second communication disconnection signal to the wireless reception unit 94 of the endoscope 80 (step Sf11). The display device control unit 103 proceeds to step Sf13.

If the communication disconnection instruction has not been received in step Sf10, the display device control unit 103 determines whether the reception information of the first communication disconnection signal has been received from the second wireless reception unit 108 (step Sf12). If the reception information of the first communication disconnection signal has not been received, the display device control unit 103 returns to step Sf2, and if the reception information of the first communication disconnection signal has been received, the display device control unit 103 proceeds to step Sf13.

The display device control unit 103 determines whether the second wireless reception unit 108 has completed the reception (step Sf13). If the second wireless reception unit 108 has not completed the reception, the second wireless reception unit 108 receives the packet data, performs a demodulation process on the received data to acquire the compressed image frame data from the packet data, and outputs the compressed image frame data to the image data storage unit 109, and the image data storage unit 109 stores the compressed image frame data (low (un-) compressed data) (step Sf14). The display device control unit 103 returns to step Sf13.

Here, the determination as to whether the second wireless reception unit 108 has completed the reception is made as follows.

First, for a determination as to whether an individual image data file has been received, information indicating a file size (file size information) is contained in the file header of the image data received by the second wireless reception unit 108. The second wireless reception unit 108 compares this file size information with a size of an actually received file to determine whether the individual image data file has been received. Alternatively, the second wireless reception unit 108 may receive the file size information from the first image data compression unit 89 of the endoscope 80 before data is received. Alternatively, the second wireless reception unit 108 may receive EOF (End Of File) information when one file has been received.

Next, for a determination as to whether all of a plurality of image data files have been received, the second wireless reception unit 108 receives file IDs from the first image data compression unit 89 of the endoscope 80 prior to image data transmission. The number of file IDs or the number of image data to be received by the second wireless reception unit is counted. If the number of image data to be received coincides with the number of actually received image data, the second wireless reception unit 108 determines that the reception has been completed. If the number of image data to be received does not coincide with the number of actually received image data, the second wireless reception unit 108 determines that the reception has not been completed. Alternatively, the second wireless reception unit 108 may receive file names or a file number instead of the file IDs.

If the reception has been completed in step Sf13, the display device control unit 103 instructs the wireless transmission unit 111 to transmit a reception completion signal, and the wireless transmission unit 111 transmits the reception completion signal to the wireless reception unit 94 of the endoscope 80 (step Sf15). The display device control unit 103 outputs an instruction for a communication disconnection from the first wireless transmission unit 90 of the endoscope 80 to the first wireless reception unit 104. The first wireless reception unit 104 disconnects the communication. Similarly, the display device control unit 103 outputs an instruction for a communication disconnection from the second wireless transmission unit 93 of the endoscope 80 to the second wireless reception unit 108. The second wireless reception unit 108 disconnects the communication. Similarly, the display device control unit 103 outputs an instruction for a communication disconnection from the wireless reception unit 94 of the endoscope 80 to the wireless transmission unit 111. Also, the display device control unit 103 outputs a communication disconnection instruction to the display device power supply unit 102. The display device power supply unit 102 causes the display device 100 to enter a standby state (step Sf16). Accordingly, the display device 100 ends the process. Further, the standby state is a state in which the display device 100 is waiting for a connection from the endoscope 80. In the standby state, the image data decompression unit 105, the image processing unit 106 and the display unit 107 stop their operations.

The communication disconnection instruction output by the display device manipulation unit 101 in step Sf10 is a signal for disconnecting the wireless communication in response to an external user manipulation. Further, the first communication disconnection signal received by the second wireless reception unit 108 in step Sf12 is a signal for disconnecting wireless communication, which is transmitted by the endoscope 80 in response to an external user manipulation. In other words, the display device manipulation unit 101 and the second wireless reception unit 108 correspond to an instructing unit for outputting a disconnection signal to disconnect the wireless communication in response to an external manipulation.

Further, after the communication disconnection instruction from the display device manipulation unit 101 or the second communication disconnection signal from the second wireless reception unit 108 is received and reception of the second image data in the second wireless reception unit 108 has been completed in step Sf13, the display device control unit 103 controls to disconnect the wireless communication in the first wireless reception unit 104 and the second wireless reception unit 108 (step Sf16).

Thus, since the endoscope 80 and the display device 100 are powered off after the second wireless reception unit 108 of the display device 100 completes the reception of the image data, it is possible to reliably acquire high-definition still image data taking time for communication.

Alternatively, only one of the endoscope manipulation unit 81 in FIG. 11 and the display device manipulation unit 101 in FIG. 12 may receive the communication disconnection instruction from the user. If only the endoscope manipulation unit 81 receives the communication disconnection instruction, the display device control unit 103 in step Sf10 of FIG. 15 always proceeds to step Sf12. Accordingly, the second communication disconnection signal is not transmitted and the endoscope control unit 83, in step Se12 of FIG. 14, always returns to step Se1 in FIG. 13, and in step Se17 of FIG. 14, always returns to step Se9. If only the display device control unit 101 receives the communication disconnection instruction, the endoscope control unit 83, in step Se11 of FIG. 14, always proceeds to step Se12 and, in step Se15, always proceeds to step Se17. Accordingly, the first communication disconnection signal is not transmitted, and the display device control unit 103, in step Sf12 of FIG. 15, always returns to step Sf2. Further, when the endoscope manipulation unit 81 receives an instruction to stop the light control unit 84 (an instruction to turn the light emitting unit 86 off), the endoscope manipulation unit 81 may output the communication disconnection instruction.

Alternatively, the endoscope 80 may transmit the second image frame data after making a communication disconnection instruction. In this case, the endoscope control unit 83 in FIG. 11 proceeds to step Se10 without making a determination as to whether a period is a highly compressed data transmission blanking period in step Se9 of FIG. 14. The display device control unit 103 in FIG. 12, in step Sf3 of FIG. 15, the second wireless reception unit 108 always proceeds to step Sf5.

Alternatively, the endoscope 80 in FIG. 11 may transmit both the highly compressed data and the low (un-) compressed data from one wireless transmission unit having both the function of the first wireless transmission unit 90 and the function of the second wireless transmission unit 93, and the display device 100 in FIG. 12 may receive both data using one wireless reception unit having both the function of the first wireless reception unit 104 and the function of the second wireless reception unit 108. In this case, for example, information for distinguishing between a highly compressed data packet and a low (un-) compressed data packet may be contained in the header of the packet so that the packets can be distinguished.

While preferred embodiments of the present invention have been described and illustrated above, it should be understood that these are exemplary of the invention and are not to be considered as limiting. Additions, omissions, substitutions, and other modifications can be made without departing from the scope of the present invention.

Further, a program for realizing the respective steps shown in FIGS. 3, 4, 8, 9, 10, 13, 14 and 15 may be recorded on a computer-readable recording medium, and may be read and executed by a computer system to perform an execution process of a communication device. Further, the "computer system" mentioned above includes an operating system (OS) or hardware such as peripheral devices.

The "computer system" also includes a homepage providing environment (or a display environment) if a WWW system is used. Further, the "computer-readable recording medium" refers to a storage unit, including a portable medium such as a flexible disk, a magnetic optical disc, a ROM, a writable nonvolatile memory such as a flash memory or a CD-ROM, or a hard disk embedded in the computer system.

The "computer-readable recording medium" includes a recording medium that holds a program for a certain time, like a volatile memory (e.g., a DRAM (Dynamic Random Access Memory)) in a computer system including a server and a client in a case in which a program is transmitted via a network such as the Internet or a communication line such as a telephone line.

Further, the program may be transmitted from a computer system that stores the program, for example, in a storage device to another computer system, via a transmission medium or by a transmission wave among transmission media. Here, the "transmission medium" for transferring the program refers to a medium having a function of transferring information, like a network (communication network) such as the Internet or a communication line (communication cable) such as a telephone line.

Further, the program may realize part of the above-described function. Further, the above-described function may be a so-called difference file (difference program) that can be realized by combination with a program that has been recorded in a computer system.

INDUSTRIAL APPLICABILITY

The present invention is very suitable for an image transmission apparatus for wirelessly transmitting image data.

DESCRIPTION OF THE REFERENCE SYMBOLS 10 endoscope
11 endoscope manipulation unit
12 endoscope power supply unit
13 endoscope control unit
14 light control unit
15 light source unit
16 light emitting unit
17 image pickup unit
18 image data generation unit
19 first image data compression unit
20 wireless transmission unit
21 second image data compression unit
22 first image data storage unit
30 display device
31 display device manipulation unit
32 display device power supply unit
33 display device control unit
34 wireless reception unit
35 image data decompression unit
36 image processing unit
37 display unit
38 second image data storage unit
39 external interface unit
40 endoscope
41 endoscope manipulation unit
42 endoscope power supply unit
43 endoscope control unit
44 light control unit
45 light source unit
46 light emitting unit
47 image pickup unit
48 image data generation unit
49 first image data compression unit
50 first wireless transmission unit
51 second image data compression unit
52 third image data storage unit
53 second wireless transmission unit
60 display device
61 display device manipulation unit
62 display device power supply unit
63 display device control unit
64 first wireless reception unit
65 image data decompression unit
66 image processing unit
67 display unit
68 second wireless reception unit
69 fourth image data storage unit
70 external interface unit
80 endoscope
81 endoscope manipulation unit
82 endoscope power supply unit
83 endoscope control unit
84 light control unit
85 light source unit
86 light emitting unit
87 image pickup unit
88 image data generation unit
89 first image data compression unit
90 first wireless transmission unit
91 second image data compression unit
92 image data storage unit
93 second wireless transmission unit
100 display device
101 display device manipulation unit
102 display device power supply unit
103 display device control unit
104 first wireless reception unit
105 image data decompression unit
106 image processing unit 107 display unit
108 second wireless reception unit
109 image data storage unit
110 external interface unit

The invention claimed is:

1. An image transmission apparatus for wirelessly communicating with an external apparatus, comprising:
   an image pick-up unit configured to output a pixel signal corresponding to an amount of incident light;
   a first image data compression unit configured to compress an image frame data, which corresponds to the pixel signal output from the image pick-up unit, by a lossy compression to output a compressed image frame data;
   a second image data compression unit configured to compress the image frame data by a lossy compression, which is at a lower compression rate than the lossy compression by the first image data compression unit, to output a compressed image frame data, or to output the image frame data that is uncompressed or compressed by a lossless compression;
   a transmission unit configured to wirelessly transmit the compressed image frame data, which has been compressed by the lossy compression and output by the first image data compression unit, as a first image data to the external apparatus through wireless communication, the transmission unit being configured to wirelessly transmit the compressed image frame data, which has been compressed by the lossy compression and output by the second image data compression unit, or the image frame data, which is uncompressed or compressed by the lossless compression and output by the second image data compression unit as a second image data;
   a manipulation unit configured to output a disconnection signal to disconnect a wireless communication by the transmission unit in response to an external manipulation; and
   a control unit configured to receive the disconnection signal from the manipulation unit and before instructing the transmission unit to disconnect the wireless communication in response to the disconnection signal, determining whether the transmission of the second image data by the transmission unit has been completed and instructing the transmission unit to complete the transmission of the second image data if the transmission of the second image data has not been completed and after completion of the transmission of the second image data, instructing the transmission unit to disconnect the wireless communication with the external apparatus.

2. The image transmission apparatus according to claim 1, wherein the control unit immediately disconnects the wireless communication if the control unit receives the disconnection signal, which has been output from the manipulating unit, during the transmission of the first image data.

3. The image transmission apparatus according to claim 2, further comprising:
   a power supply unit configured to supply power to the image transmission apparatus, and
   wherein the control unit configured to stop power supply from the power supply unit after receiving the disconnection signal from the manipulation unit and completing the transmission of the second image data by the transmission unit.

4. The image transmission apparatus according to claim 1, wherein
   the control unit is configured to disconnect the wireless communication after receiving the disconnection signal from the manipulation unit and receiving a reception completion signal, which indicates that transmission of the second image data has been completed, from a terminal that wirelessly receives the second image data wirelessly transmitted from the transmission unit.

5. The image transmission apparatus according to claim 1, wherein
   the control unit is configured to disconnect the wireless communication by the transmission unit after receiving the disconnection signal from the manipulation unit and transmission of all of the second image data, which have been output from the second image data compression unit, has been completed.

6. The image transmission apparatus according to claim 1, wherein
   the transmission unit is configured to wirelessly transmit a number data indicating the number of the second image data that is to be wirelessly transmitted before wirelessly transmitting the second image data, and the control unit is configured to control to disconnect the wireless communication after receiving the disconnection signal from the manipulation unit and transmission by the transmission unit of wirelessly receiving a signal, which indicates wireless receptions of all of the second image data has been completed by referring to the number data, has been completed.

7. An image reception apparatus for wirelessly communicating with an external apparatus, comprising:
   a reception unit configured to wirelessly receive a first image data that is an image frame data compressed by a first lossy compression from the external apparatus through wireless communication, the reception unit being configured to wirelessly receive a second image data, the second image data being an image frame data that is compressed by a second lossy compression at a lower compression rate than the first lossy compression or an image frame data that is uncompressed or compressed by a lossless compression;
   a manipulation unit configured to output a disconnection signal to disconnect the wireless communication by the reception unit in response to an external manipulation; and
   a control unit configured to receive the disconnection signal from the manipulation unit and before instructing the reception unit to disconnect the wireless communication in response to the disconnection signal, determining whether the reception of the second image data by the reception unit has been completed and instructing the reception unit to complete the reception of the second image data if the reception of the second image data has not been completed and after completion of the reception of the second image data, instructing the reception unit to disconnect the wireless communication with the external apparatus, the control unit configured to output a standby signal to a power supply unit to put the image reception apparatus in a standby mode.

8. The image reception apparatus according to claim 7, wherein the reception unit is configured to wirelessly receive a number data indicating the number of the second image data that is to be wirelessly transmitted from the external apparatus before wirelessly receiving the second image data, and
   the control unit is configured to determine whether or not wireless receptions of all of the second image data, which are wirelessly transmitted from the external apparatus, has been completed based on a number indicated by the number data and the number of the second image data that are wirelessly received, the control unit being configured to disconnect the wireless communication after receiving the disconnection signal from the manipulation unit and determining that wireless receptions of all of the second image data has been completed by referring to the number data.

9. An image transmission method for wirelessly communicating with an external apparatus, comprising:
- a first step of compressing an image frame data, which corresponds to a pixel signal corresponding to an amount of incident light, by a lossy compression to output a compressed image frame data;
- a second step of compressing the image frame data by a lossy compression, which is at a lower compression rate than the lossy compression by the first step, to output a compressed image data, or outputting the image frame data that is uncompressed or compressed by a lossless compression,
- a third step of wirelessly transmitting the compressed image frame data, which has been compressed by the lossy compression and output by the first step, as a first image data to the external apparatus through wireless communication,
- a fourth step of wirelessly transmitting the compressed image frame data, which has been compressed by the lossy compression and output by the second step or the image frame data that is uncompressed or compressed by the lossless compression by the second step, as a second image data to the external apparatus through wireless communication,
- a fifth step of outputting a disconnection signal to disconnect a wireless communication by the third step and the fourth step in response to an external manipulation, and
- a sixth step of receiving the disconnection signal outputted by the fifth step and before instructing to disconnect the wireless communication in response to the disconnection signal, determining whether the transmission of the second image data by the fourth step has been completed and completing the transmission of the second image data if the transmission of the second image data by the fourth step has not been completed and after completion of the transmission of the second image data by the fourth step, disconnecting the wireless communication with the external apparatus.

10. A non-transitory computer-readable recording device storing computer-executable instructions that when executed by one or more processors causes said one or more processors to perform the image transmission method according to claim 9.

11. An image reception method for wirelessly communicating with an external apparatus comprising:
- a first step of wirelessly receiving a first image data that is an image frame data compressed by a first lossy compression;
- a second step of wirelessly receiving a second image data, the second image data being an image frame data that is compressed by a second lossy compression at a lower compression rate than the first lossy compression by the first step or an image frame data that is uncompressed or compressed by a lossless compression from the external apparatus through wireless communication;
- a third step of outputting a disconnection signal to disconnect a wireless communication by the first step and the second step in response to an external manipulation;
- a fourth step of receiving the disconnection signal outputted by the third step and before instructing to disconnect the wireless communication in response to the disconnection signal, determining whether the reception of the second image data by the second step has been completed and completing the reception of the second image data if the reception of the second image data by the second step has not been completed and after completion of the reception of the second image data by the second step, disconnecting the wireless communication with the external apparatus; and
- a fifth step of outputting a standby signal to put the image reception by the first and second step in a standby mode.

12. A non-transitory computer-readable recording device storing computer-executable instructions that when executed by one or more processors causes said one or more processors to perform the image transmission method according to claim 11.

* * * * *